(12) United States Patent
Bergey

(10) Patent No.: US 11,701,238 B2
(45) Date of Patent: *Jul. 18, 2023

(54) COMPRESSIVE, ORTHOPEDIC, ANCHORING APPARATUS AND METHOD

(71) Applicant: Darren L. Bergey, Riverside, CA (US)

(72) Inventor: Darren L. Bergey, Riverside, CA (US)

( * ) Notice: Subject to any disclaimer, the term of this patent is extended or adjusted under 35 U.S.C. 154(b) by 631 days.

This patent is subject to a terminal disclaimer.

(21) Appl. No.: 16/838,827

(22) Filed: Apr. 2, 2020

(65) Prior Publication Data

US 2020/0246158 A1 Aug. 6, 2020

Related U.S. Application Data

(60) Continuation-in-part of application No. 16/263,405, filed on Jan. 31, 2019, now Pat. No. 10,898,345, (Continued)

(51) Int. Cl.
*A61F 2/44* (2006.01)
*A61F 2/30* (2006.01)
*A61F 2/28* (2006.01)

(52) U.S. Cl.
CPC ............ *A61F 2/447* (2013.01); *A61F 2/4425* (2013.01); *A61F 2/4455* (2013.01); *A61F 2/4465* (2013.01); *A61F 2002/2817* (2013.01); *A61F 2002/2835* (2013.01); *A61F 2002/3023* (2013.01); *A61F 2002/30187* (2013.01);
(Continued)

(58) Field of Classification Search
CPC ......... A61F 2/447; A61B 17/846; F16B 15/06
See application file for complete search history.

(56) References Cited

U.S. PATENT DOCUMENTS

| 1,635,923 A | 7/1927 | Bray |
| 6,128,867 A | 10/2000 | MacKarvich |

(Continued)

FOREIGN PATENT DOCUMENTS

| CA | 2758922 A1 | 10/2010 |
| CN | 1244105 A | 2/2000 |

(Continued)

OTHER PUBLICATIONS

American Society for Reproductive Medicine, Adhesion Prevention: A Standard of Care, Surgical Techniques and Cost Effectiveness of Adhesion Prevention, Aug. 20, 2014.

(Continued)

*Primary Examiner* — Andrew Yang
(74) *Attorney, Agent, or Firm* — Pate Nelson & Hill, PLLC

(57) ABSTRACT

A long-pitch, helical anchor includes splines radially extending and helically progressing circumferentially around and along the arcuate length of a curved center line (central curve). The center line may progress along the curved length of the anchor with all splines meeting near the center line. In other embodiments, the center line passes along the center of a lumen or channel from which the splines extend radially along the length. A solid point acts as a cutting edge on a distal end of the anchor. All the splines converge to the center line. Installation may be with or without a stabilizing frame, such as may be used to fill gaps and promote bone growth between joined members. The anchors may be used directly to connect and provide compression between two bones or bone structures.

20 Claims, 27 Drawing Sheets

Related U.S. Application Data which is a division of application No. 15/380,048, filed on Dec. 15, 2016, now Pat. No. 10,195,051, which is a division of application No. 15/001,502, filed on Jan. 20, 2016, now Pat. No. 9,539,110, which is a division of application No. 13/937,208, filed on Jul. 8, 2013, now Pat. No. 9,248,029, which is a continuation of application No. PCT/US2012/020560, filed on Jan. 6, 2012.

(60) Provisional application No. 61/430,296, filed on Jan. 6, 2011.

(52) U.S. Cl.
CPC ........... *A61F 2002/30578* (2013.01); *A61F 2002/30593* (2013.01); *A61F 2002/30607* (2013.01); *A61F 2002/30616* (2013.01); *A61F 2002/30782* (2013.01); *A61F 2002/30787* (2013.01); *A61F 2002/30841* (2013.01); *A61F 2002/30878* (2013.01); *A61F 2002/30904* (2013.01); *A61F 2310/00023* (2013.01); *A61F 2310/00161* (2013.01)

(56) References Cited

U.S. PATENT DOCUMENTS

| | | | |
|---|---|---|---|
| 6,432,106 | B1 | 8/2002 | Fraser |
| 8,142,508 | B1 | 3/2012 | Bruffey et al. |
| 8,167,949 | B2 | 5/2012 | Tyber et al. |
| 8,267,997 | B2 | 9/2012 | Colleran |
| 8,292,958 | B1 | 10/2012 | Bruffey et al. |
| 8,353,938 | B2 | 1/2013 | Trieu et al. |
| 8,366,774 | B1 | 2/2013 | Bruffey et al. |
| 8,414,651 | B2 | 4/2013 | Tyber et al. |
| 8,460,294 | B2 | 6/2013 | Overes |
| 8,500,784 | B2 | 8/2013 | Hulliger et al. |
| 8,506,534 | B2 | 8/2013 | Marnay et al. |
| 8,523,916 | B2 | 9/2013 | Anderson et al. |
| 8,568,483 | B2 | 10/2013 | Coppes et al. |
| 8,579,903 | B2 | 11/2013 | Carl |
| 8,579,978 | B2 | 11/2013 | Marnay et al. |
| 8,591,513 | B2 | 11/2013 | Overes et al. |
| 8,603,144 | B2 | 12/2013 | Kwak et al. |
| 8,617,225 | B2 | 12/2013 | McShane et al. |
| 8,623,057 | B2 | 1/2014 | Jahng et al. |
| 8,641,734 | B2 | 2/2014 | Moumene et al. |
| 8,641,766 | B2 | 2/2014 | Donner et al. |
| 8,647,347 | B2 | 2/2014 | Runco et al. |
| 8,663,229 | B2 | 3/2014 | Marnay et al. |
| 8,663,292 | B2 | 3/2014 | Dec et al. |
| 8,663,298 | B2 | 3/2014 | Keyer et al. |
| 8,679,162 | B2 | 3/2014 | Strausbaugh et al. |
| 8,685,066 | B2 | 4/2014 | Stad et al. |
| 8,685,104 | B2 | 4/2014 | Lee et al. |
| 8,696,703 | B2 | 4/2014 | Anspach, III et al. |
| 8,721,692 | B2 | 5/2014 | Anderson et al. |
| 8,734,490 | B2 | 5/2014 | Anderson et al. |
| 8,740,946 | B2 | 6/2014 | Peterson et al. |
| 8,757,035 | B2 | 6/2014 | Kerboul et al. |
| 8,771,271 | B2 | 7/2014 | Overes |
| 8,777,960 | B2 | 7/2014 | Murray et al. |
| 8,795,371 | B2 | 8/2014 | Marnay et al. |
| 8,828,007 | B2 | 9/2014 | Stad et al. |
| 8,845,697 | B2 | 9/2014 | Montello et al. |
| 8,845,700 | B2 | 9/2014 | Kwak et al. |
| 2006/0085071 | A1 | 4/2006 | Lechmann |
| 2011/0098747 | A1 | 4/2011 | Donner et al. |
| 2011/0230971 | A1 | 9/2011 | Donner et al. |

FOREIGN PATENT DOCUMENTS

| | | |
|---|---|---|
| CN | 101442944 B | 5/2009 |
| EP | 0427906 A1 | 5/1991 |
| EP | 2361573 A2 | 8/2011 |

OTHER PUBLICATIONS

SprayShield.org, Informations about adhesions barriers and SprayShield Adhesion barrier, the new product by Covidien, Oct. 2011.
Women's Surgery Group, Adhesion Overview, Aug. 21, 2014.
The American Journal of Surgery, Peritoneal adhesions and their relation to abdominal surgery, vol. 126, Issue 3, pp. 345-353, Sep. 1973.
British Journal of Surgery Society Ltd, Morbidity and mortality of inadvertent enterotomy during adhesiotomy, vol. 87, Issue 4, Apr. 2000, published online Dec. 6, 2002.
American Academy of Orthopaedic Surgeons, Choosing Wisely, An Initiative of the ABIM Foundation, Sep. 11, 2013.
Human Reproduction Update, Clinical implications of postsurgical adhesions, vol. 7, No. 6, pp. 567-576, 2001.
Surgery: a retrospective cohort study, vol. 353, Issue 9163, pp. 1476-1480, 1999.
PubMed NCBI, Peritoneal adhesions; etiology, pathophysiology, and clinical significance. Recent advances in prevention and management Dig. Surg. 2001: 18(4):260-73.
MedicineNet.com, Abdominal Adhesions (Scar Tissue), Aug. 20, 2014.
Better Health Channel, Fact Sheet, Adhesions, Aug. 20, 2014.
Journal of Surgical Research, Heated and Humidified CO, Prevents Hypothermia, Peritoneal Injury, and Intra-Abdominal Adhesions During Prolonged Laparoscopic Insufflations, vol. 152, Issue 1, pp. 40-47, Jan. 2009, published online May 12, 2008.
Oxford Journals, Medicine and Health, Human Reproduction Update, vol. 19, Issue 1, pp. 12-25, Jan./Feb. 2013, published online Aug. 16, 2012.
Synechion, Inc., Adhesions Related Disease-Adhesions Related Deaths, Sep. 23, 2003.
PubMed NCBI, Histologic study of peritoneal adhesions in children and in rat model, Pediatr Surg Int. Dec. 2002; 18(8):676-6, Epub Sep. 24, 2002.
Human Reproduction Update, Peritoneal repair and post-surgical adhesion formation, vol. 7, No. 6, pp. 547-555, 2001.

COMPRESSIVE, ORTHOPEDIC, ANCHORING APPARATUS AND METHOD

RELATED APPLICATIONS

This application: is a continuation-in-part of U.S. patent application Ser. No. 16/263,405, filed Jan. 31, 2019; which is a divisional application of U.S. patent application Ser. No. 15/380,048, filed Dec. 15, 2016, issued as U.S. Pat. No. 10,195,051 on Feb. 5, 2019; which is a divisional application of U.S. patent application Ser. No. 15/001,502, filed Jan. 20, 2016, issued as U.S. Pat. No. 9,539,110 on Jan. 10, 2017; which is a divisional application of U.S. patent application Ser. No. 13/937,208, filed Jul. 8, 2013, issued as U.S. Pat. No. 9,248,029 on Feb. 2, 2016; which is a continuation of PCT Application Serial No. PCT/US2012/020560, filed Jan. 6, 2012; which claims the benefit of U.S. Provisional Patent Application Ser. No. 61/430,296, filed Jan. 6, 2011. All the foregoing references are hereby incorporated herein by reference.

BACKGROUND

Field of the Invention

This invention relates to orthopedic surgery and, more particularly, to novel systems and methods for anchoring to and between bone structures.

Background Art

Orthopedic surgery has long depended on unique instruments and unique securement arrangements in order to encourage healing of fractures, regrowth of bone structures, and the like. Various securement mechanisms involve combinations of plates and screws, sometimes rods, and various other hardware.

Bones have a structure that is harder around the outside envelope (boundary) thereof, called cortical bone. Meanwhile, enclosed therewithin is medullar bone, sometimes called cancellous bone. Cancellous bone hosts the marrow and vasculature associated therewith. Consequently, the bone itself is quite porous and sparse, sometimes referred to as "spongey." Cancellous or medullar bone material has less actual structural material forming around vacuoles containing soft tissues (marrow, vasculature, etc.). It has reduced ability to maintain embedded rigidly therein a conventional thread of a screw.

Meanwhile, thread pitch is of the same order of magnitude as the height of the threads from the shank (solid shaft) of a screw. Thus, the actual "purchase" (physical engagement or contact between the screw and the structural material of the bone) is much less in the cancellous bone than in the cortical bone. However, the cortical bone is comparatively thin, typically, or a comparatively small fraction of many bones or bone structures and length of screws anchored therein.

That is, just as in wood, threads on a screw or similar hardware may simply shear (core out) the corresponding threads they cut into the receiving bone. Thus, pull-out strength may be severely compromised by the spiraling threads with their intermediate bone material therebetween. It would be an advance in the art to provide a more secure form of anchoring. It would be an advance in the art to provide anchors capable of securing into cortical bone and cancellous bone with reduced risk of simply "coring" out.

Meanwhile, bone regrowth or "through growth" around and through foreign objects such as screws, plates, spacers, or the like is to be promoted. It would be an advance in the art to improve spaces for "through growth" through spacers or frames used with anchors in various types of surgery.

It would be an advance in the art to provide anchors capable of securing one bone structure to another in order to promote joinder therebetween. It would be an advance in the art likewise to provide both spacers and anchors having apertures, porosity, highly textured surfaces, and the like in order to provide more shear strength, as opposed to mere friction securing new bone growth to spacers, anchors, and so forth.

BRIEF SUMMARY OF THE INVENTION

In view of the foregoing, in accordance with the invention as embodied and broadly described herein, a method and apparatus are disclosed in one embodiment of the present invention as including an anchor selected from several types that may be directly driven (malleted) rather than screwed with a driver. Anchors may include a central aperture or channel along a center line, where the center line is itself curved, such as on a radius or arc. In certain embodiments, the anchors may include splines. The splines may parallel the center line (center curve) as they extend radially away from a wall of a central channel or core. Splines may each progress helically in a comparatively long pitch, helical direction. By "long pitch" is meant that the pitch is typically multiple diameters, and even multiple lengths long. Pitch represents a distance traversed by a flute (where a flute may be a thread or a spline) per revolution of rotational progress. The twist (distance per revolution) in a conventional screw is typically sufficiently small that a full 360 degree rotation (two pi radians, or $2\times\pi$ radians) occurs at a fraction of the diameter distance.

For example, a one quarter by 20 (¼×20) bolt or screw has a one quarter inch diameter in which 20 threads or 20 revolutions of the threads occur in every inch of length. This means an inch of axial progress occurs in 20 complete circles or complete spirals of the threads. In contrast, an anchor in accordance with the invention has a pitch that is typically several lengths (even up to dozens of diameters) of the fastener or anchor.

Splines are angled primarily to travel along their length, while progressing along a helical path that will typically not make a full revolution within the entire length, or even a few lengths, but many (e.g., four, six, eight, or more).

Thus, such splines will typically make less than one quarter (usually from one sixth to one tenth) of a revolution or progress about the circumference within the entire length. Meanwhile the aspect ratio of diameter to length is itself less than a fifth to a tenth (1:5 to 1:10). In fact, the progression or the amount of angle traversed circumferentially is typically on the order of only one eighth (⅛) of the circumference or less.

Thus, anchors in accordance with the invention may be malleted (driven axially by impact loading) into place. Spiraling and twisting by the splines moves the anchor through the cortical bone and along both an arcuate centerline and a helical path through the cancellous bone therewithin. The result is that only a small fraction of the spline surface area aligns parallel to the pull-out direction (back toward the head. Thus, the splines resist any force tending to pull out, while they themselves present a significantly greater surface area and less load (pressure, force per unit area) against the cancellous bone than does a conventional screw.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 7F is a side elevation view thereof, in a plane perpendicular to the curvature of the curved central axis.

DETAILED DESCRIPTION OF THE PREFERRED EMBODIMENTS

Figure 1A:
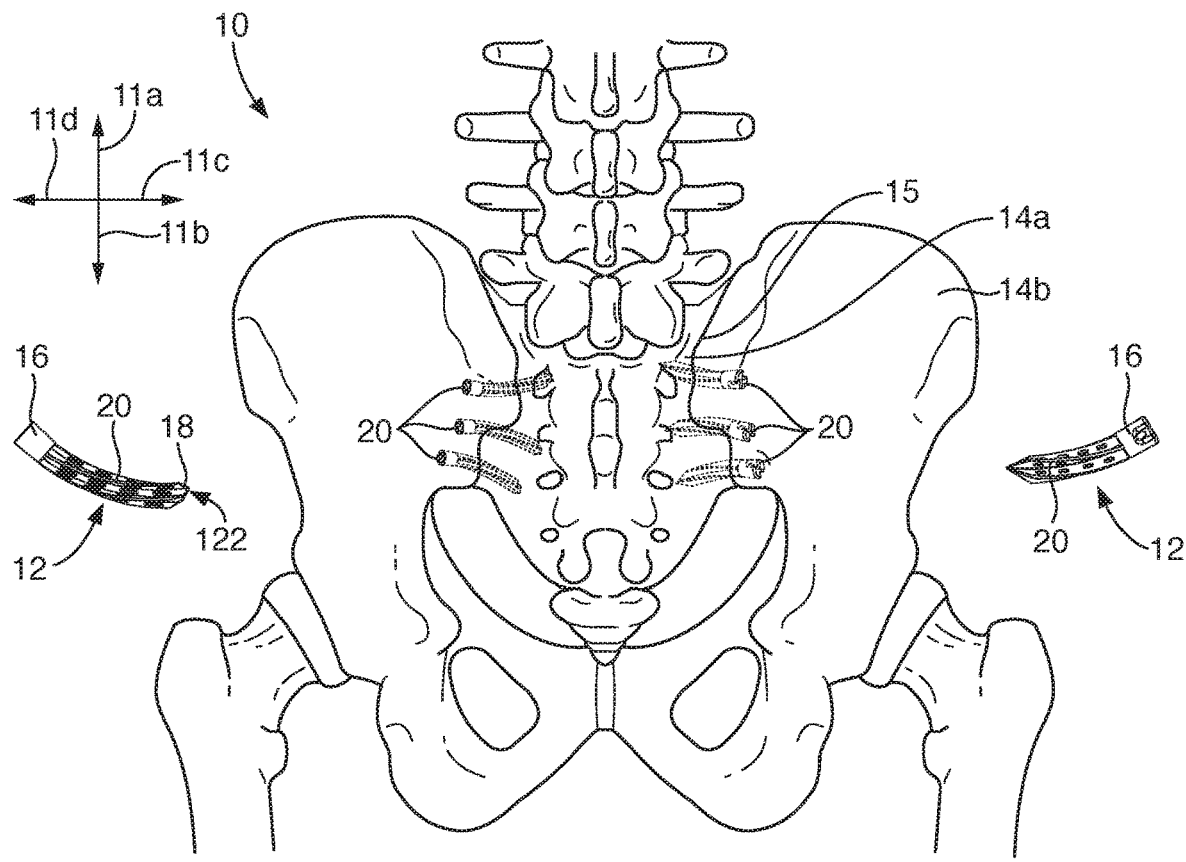
FIG. 1A is a posterior (rear elevation) view of a sacroiliac (SI) joint fusion relying on three anchors for each joint fixation, illustrating one embodiment of an anchor on the right, and another embodiment on the left, implemented in an apparatus and method in accordance with the invention.
Figure 1B:
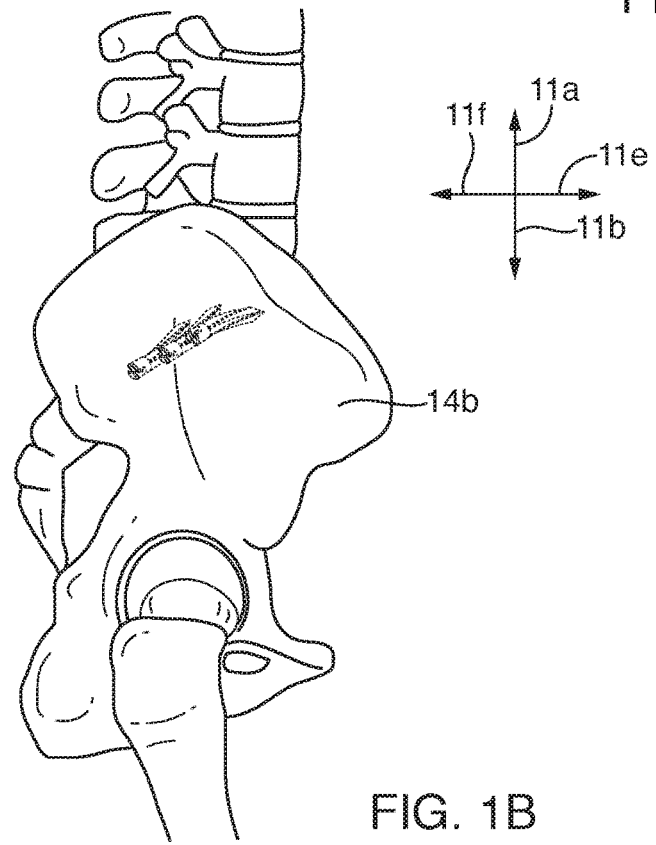
FIG. 1B is a lateral (right side elevation) view thereof, an opposite side being a mirror image thereon.
Figure 1C:
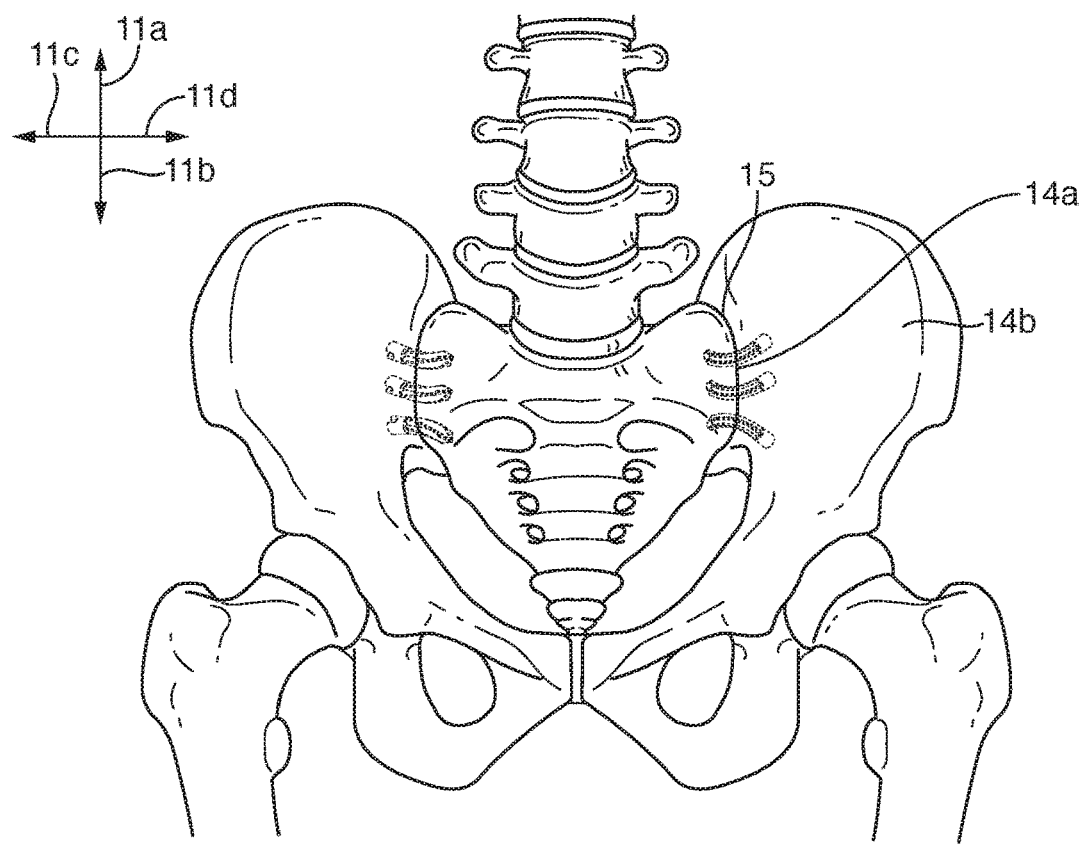
FIG. 1C is an anterior (front elevation) view thereof.
Figure 1D:
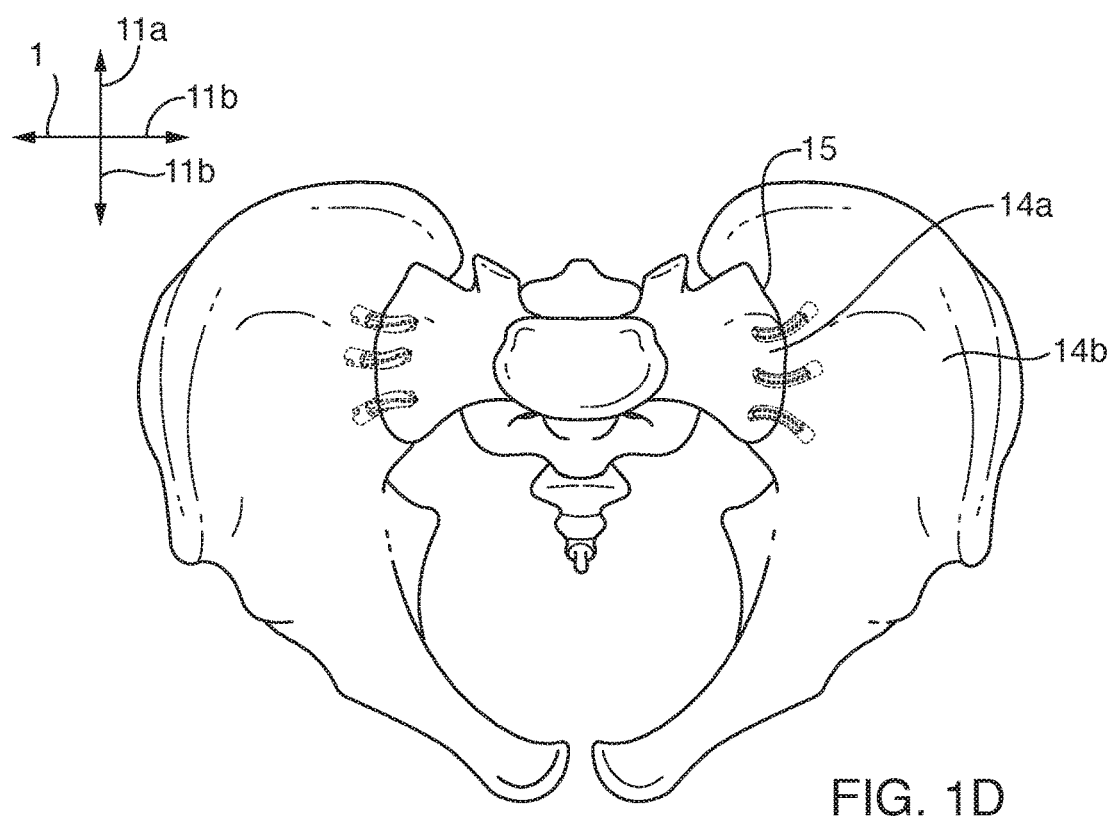
FIG. 1D is a superior (top plan) view thereof.
Figure 1E:
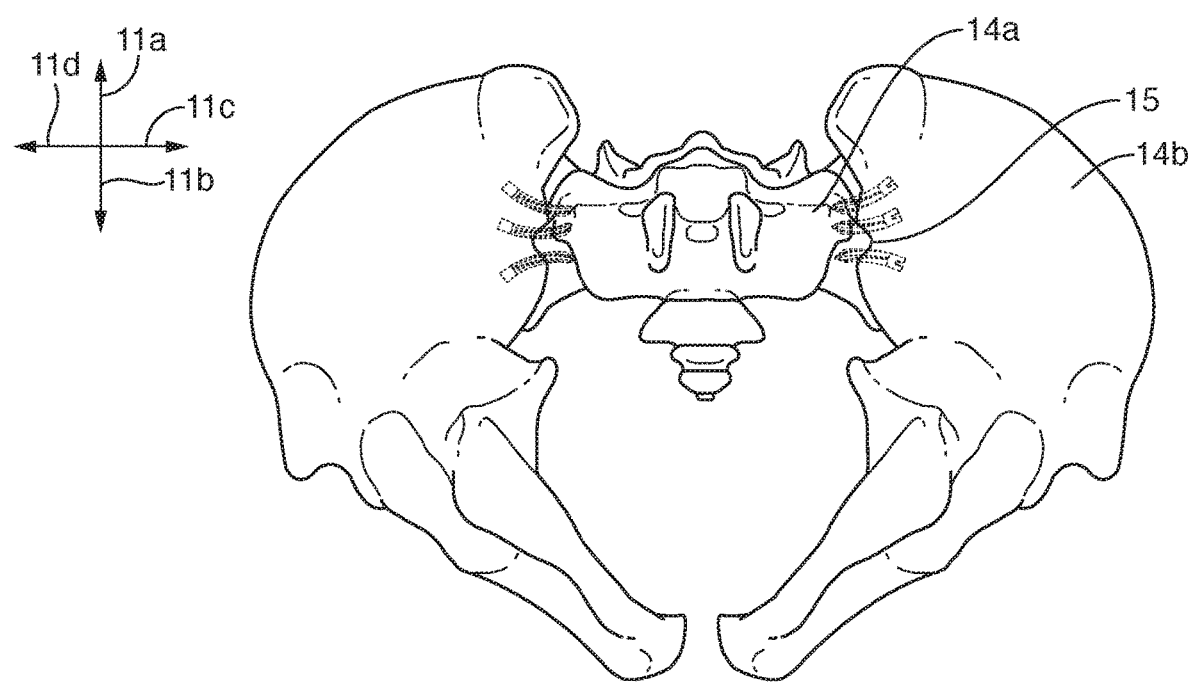
FIG. 1E is an inferior (bottom plan) view thereof.
Figure 1F:
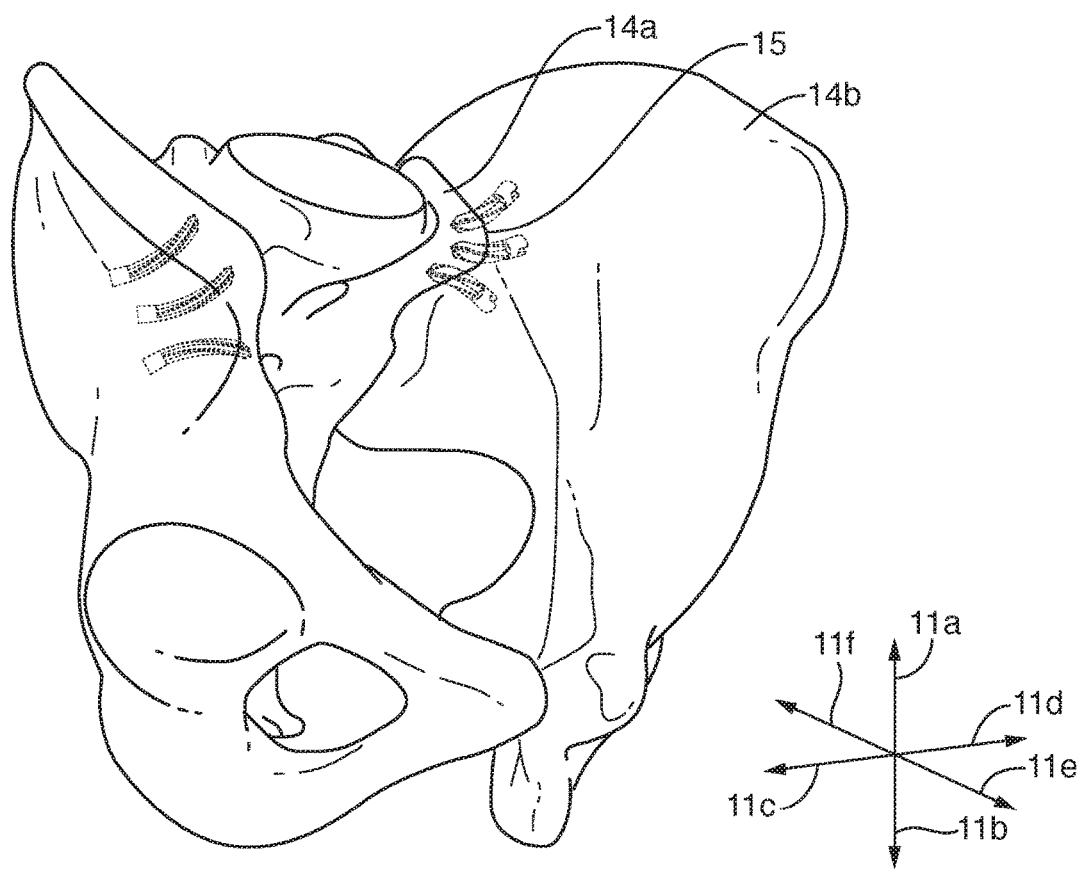
FIG. 1F is a superior and anterior (upper and frontal), perspective view thereof.
Figure 1G:
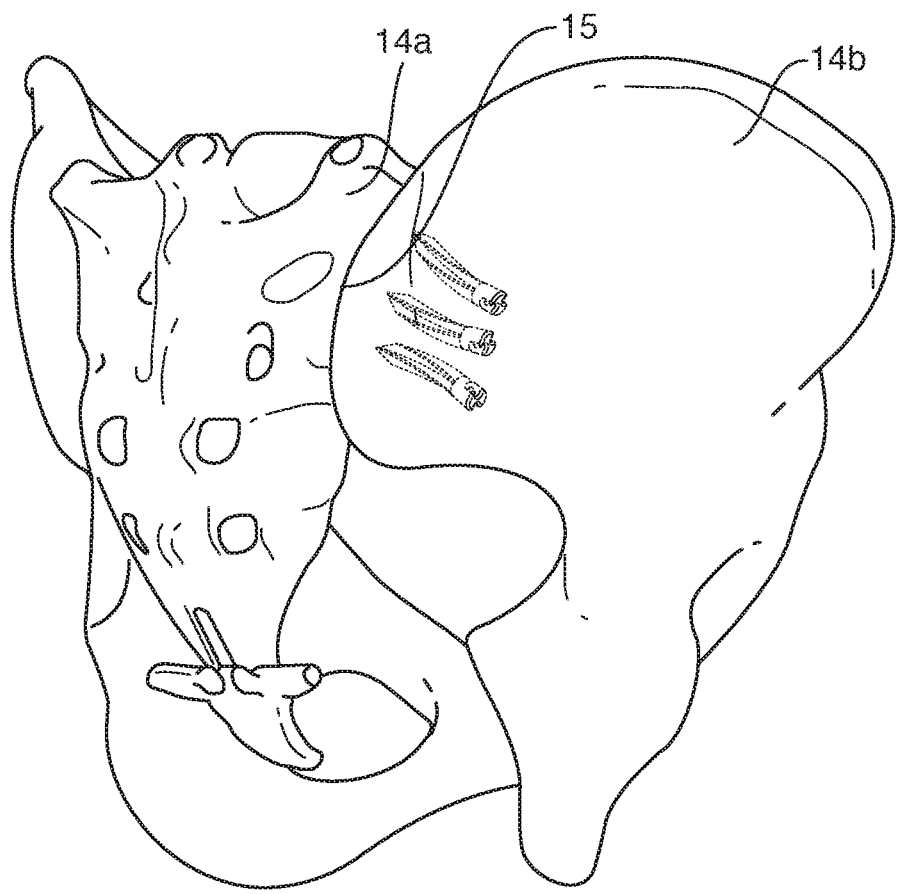
FIG. 1G is an inferior and posterior (lower and rear), perspective view thereof.
Figure 1G:
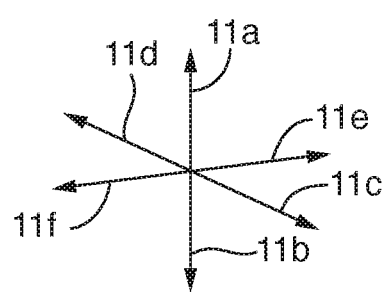
Figure 1H:
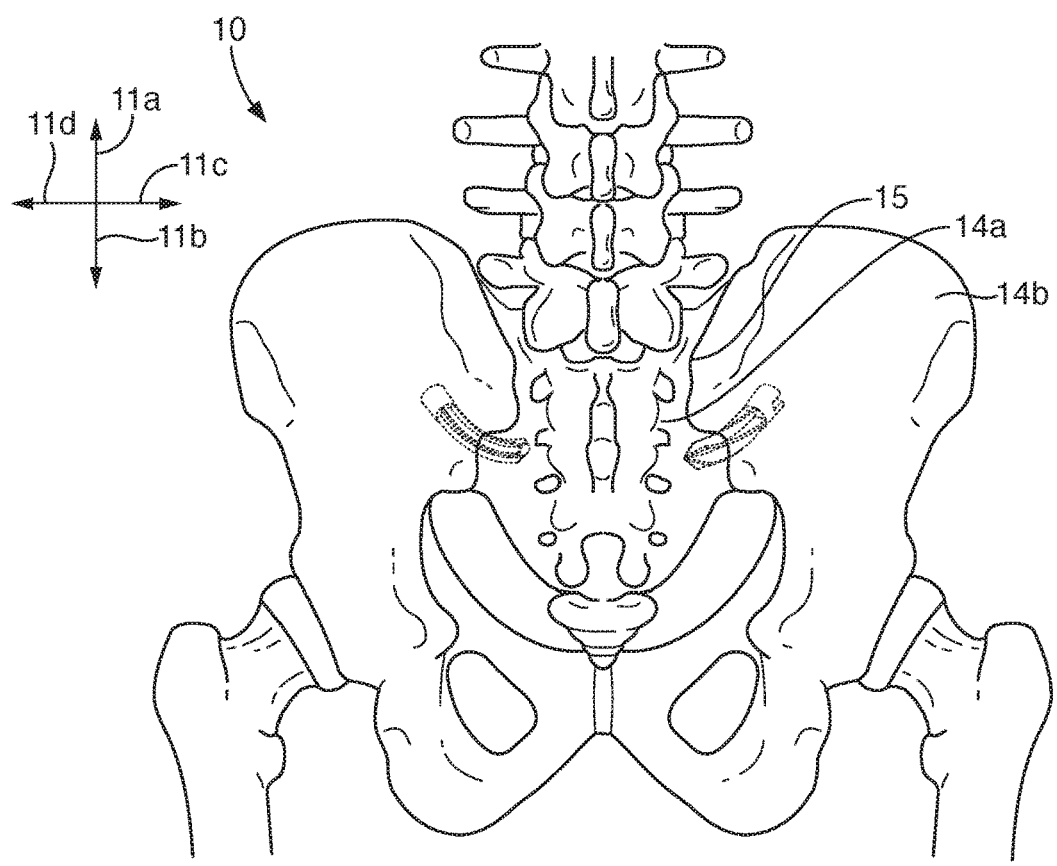
FIG. 1H is a posterior (rear elevation) view of a sacroiliac (SI) joint fusion relying on a single anchor (different embodiments shown on left and right sides) for each joint fixation in alternate embodiments of an apparatus and method in accordance with the invention.
Figure 1J:
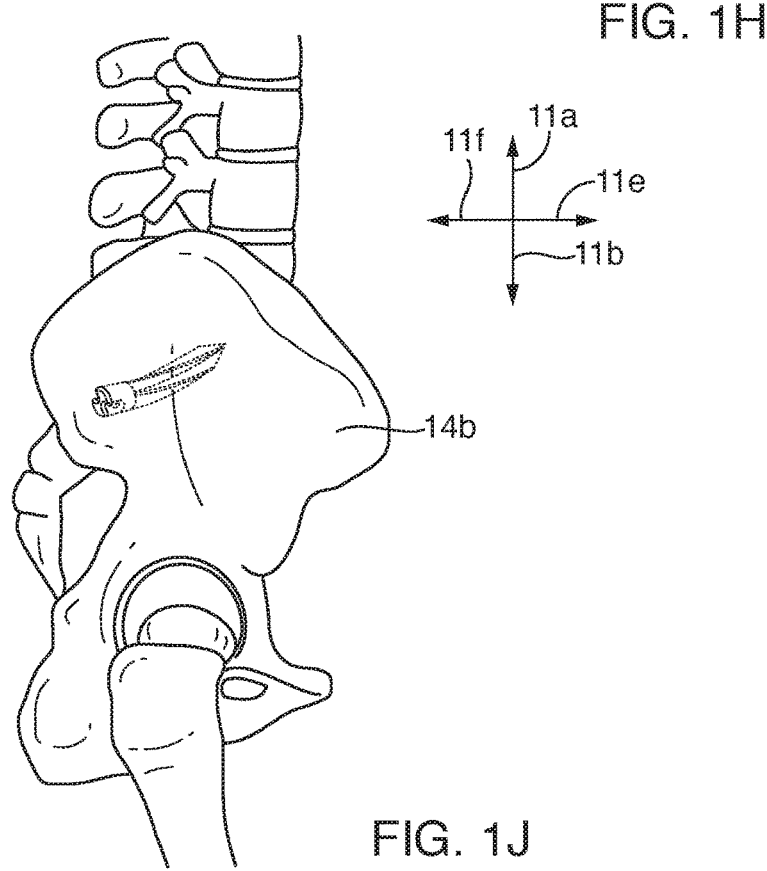
FIG. 1J is a lateral (right side elevation) view thereof, an opposite side being a mirror image thereon.
Figure 1K:
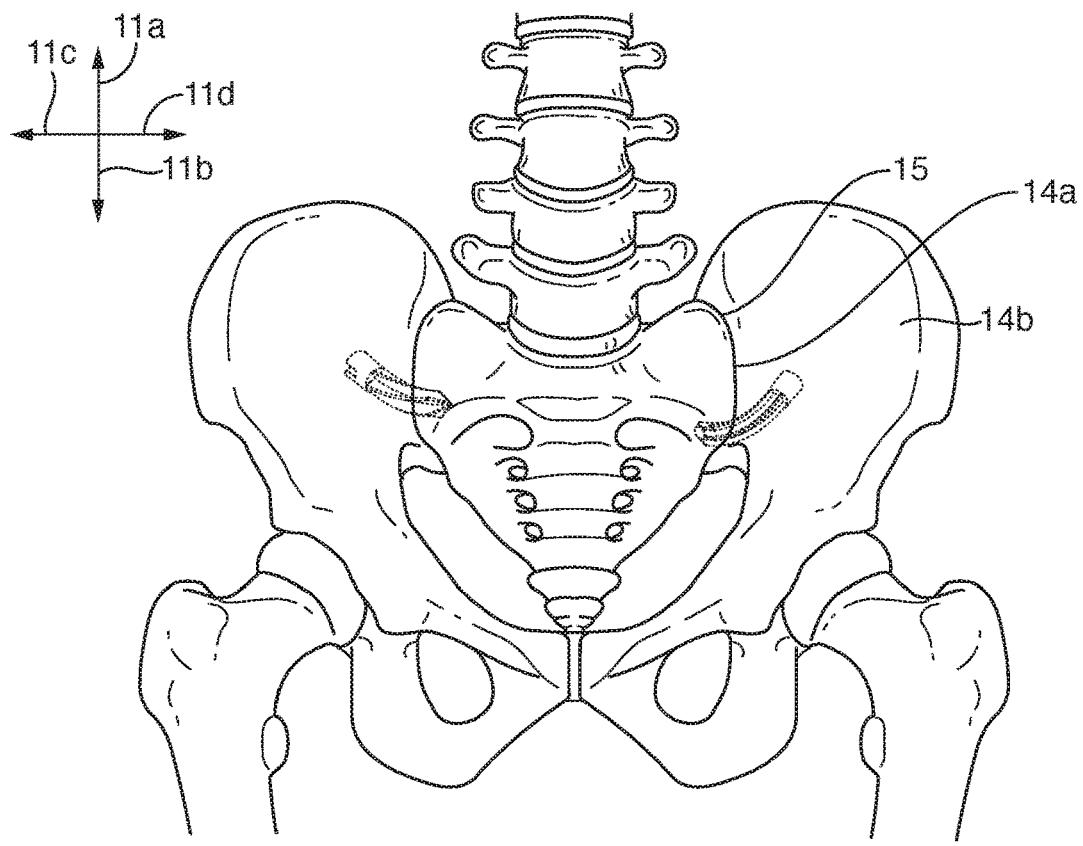
FIG. 1K is an anterior (front elevation) view thereof.
Figure 1M:
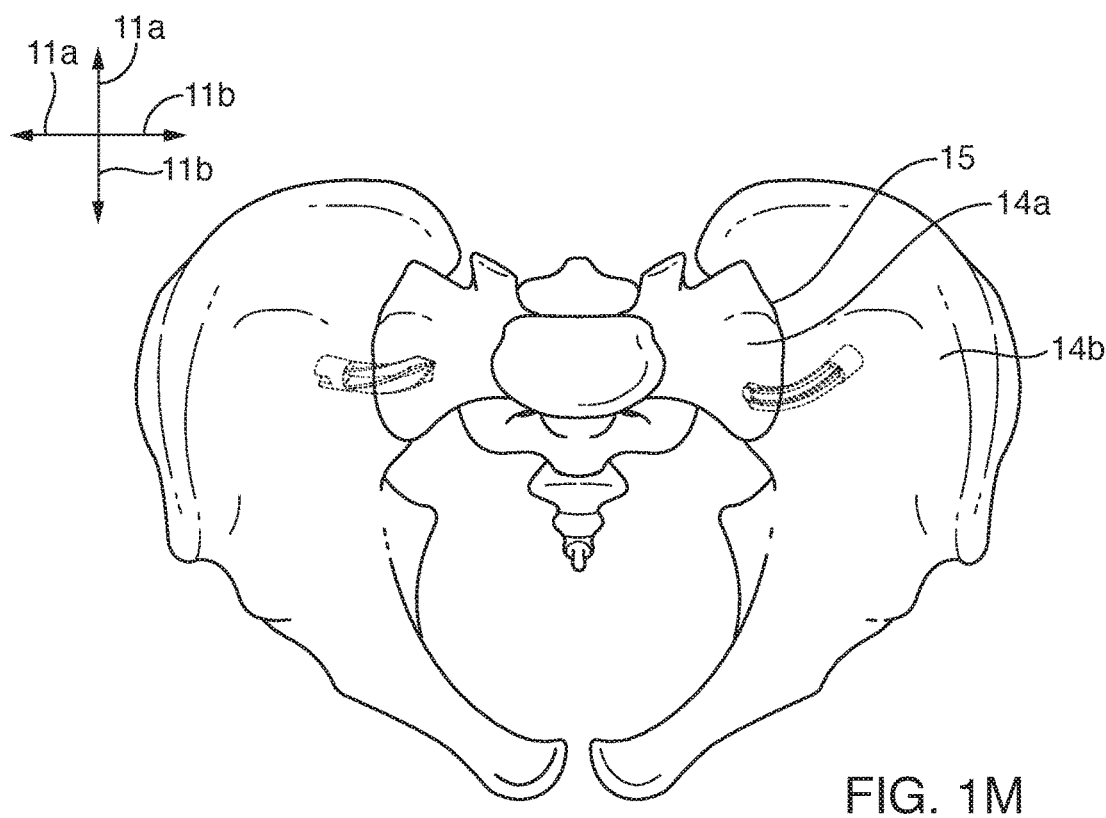
FIG. 1M is a superior (top plan) view thereof.
Figure 1N:
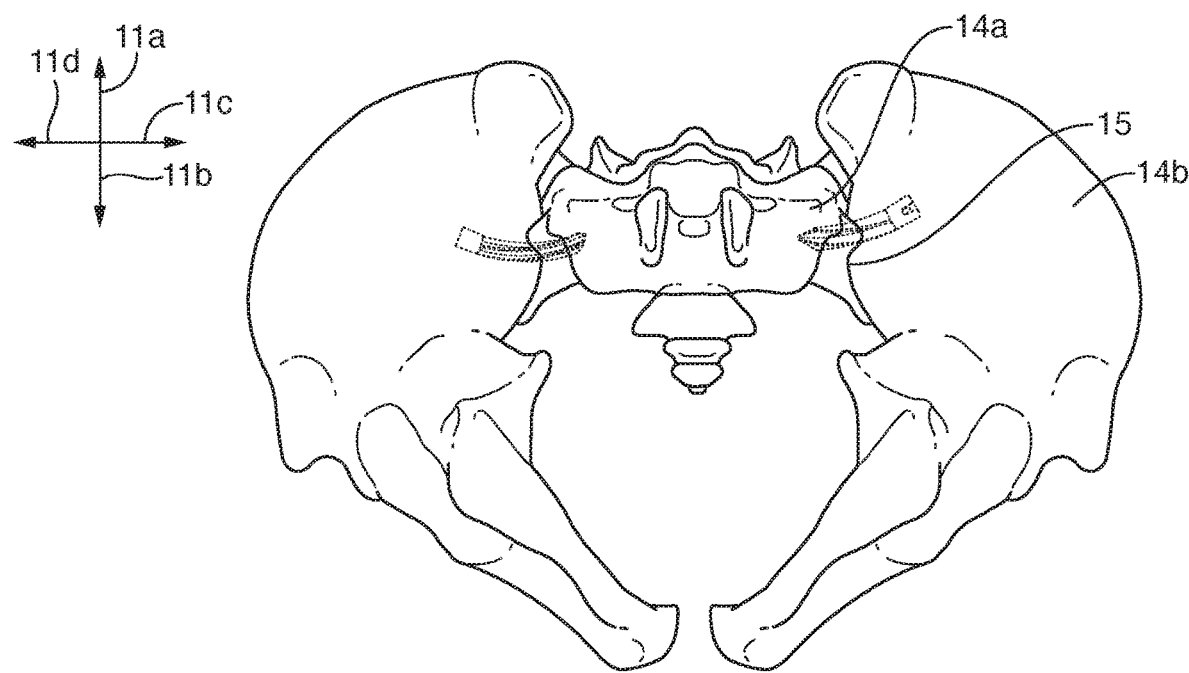
FIG. 1N is an inferior (bottom plan) view thereof.
Figure 1P:
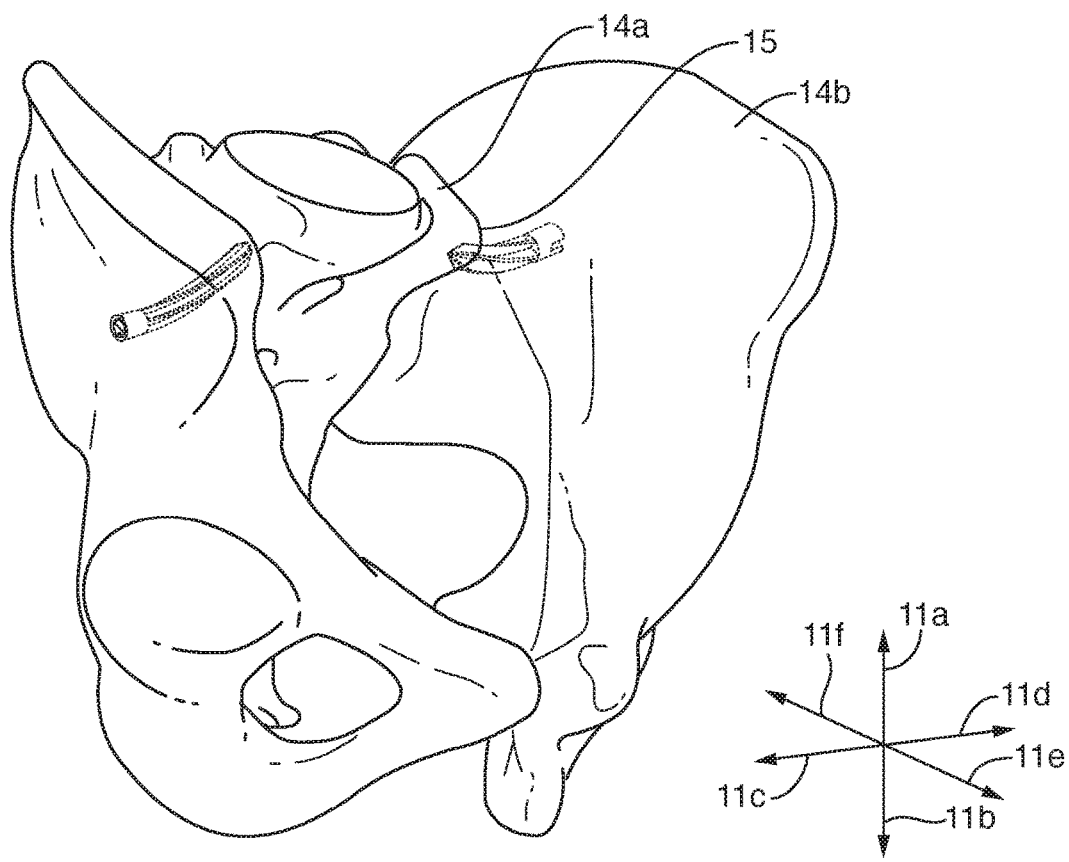
FIG. 1P is a superior and anterior (upper and frontal), perspective view thereof.
Figure 1Q:
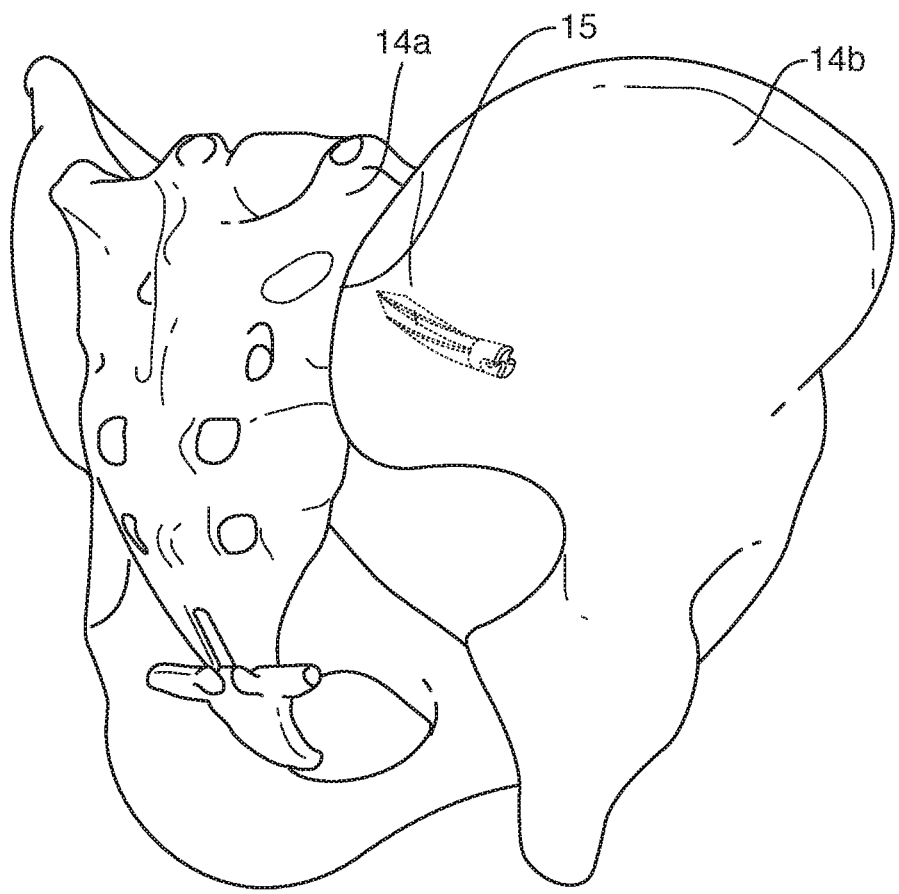
FIG. 1Q is an inferior and posterior (lower and rear), perspective view thereof.
Figure 1Q:
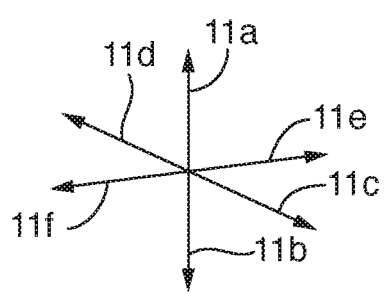
Figure 1R:
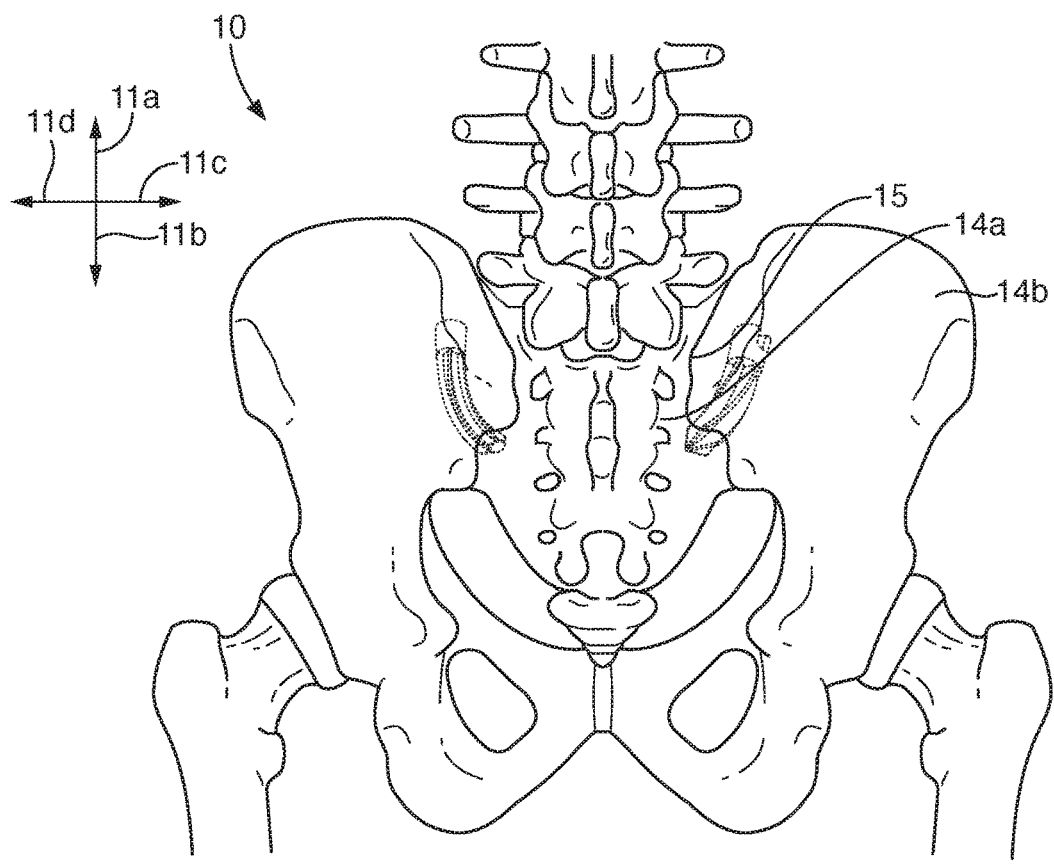
FIG. 1R is a posterior (rear elevation) view of a sacroiliac (SI) joint fusion relying on a single anchor inserted from posterior access in a joint along the direction of the joint boundary, between the sacrum and the ilium, for each joint fixation in an alternate embodiment of an apparatus and method in accordance with the invention.
Figure 1S:
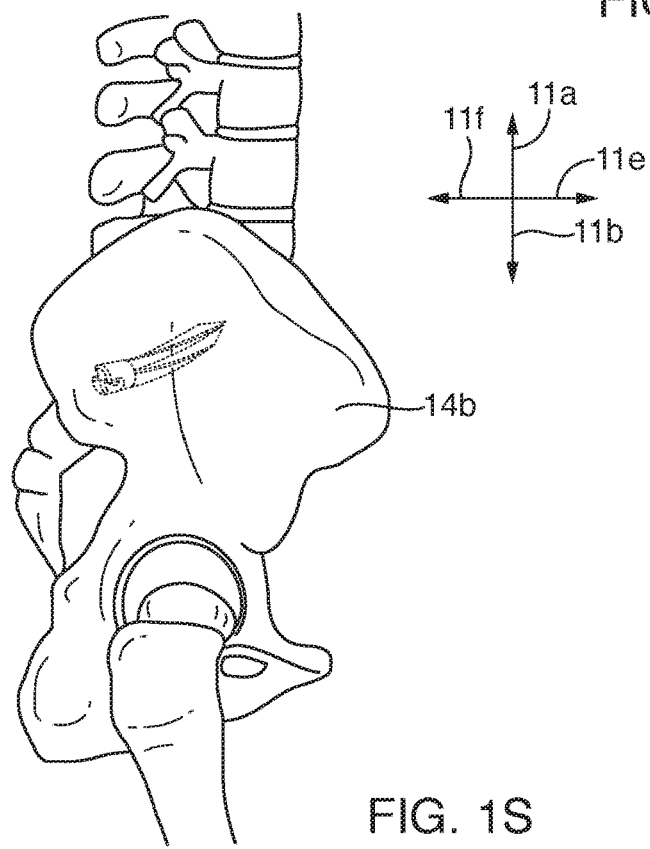
FIG. 1S is a lateral (right side elevation) view thereof, an opposite side being a mirror image thereon.
Figure 1T:
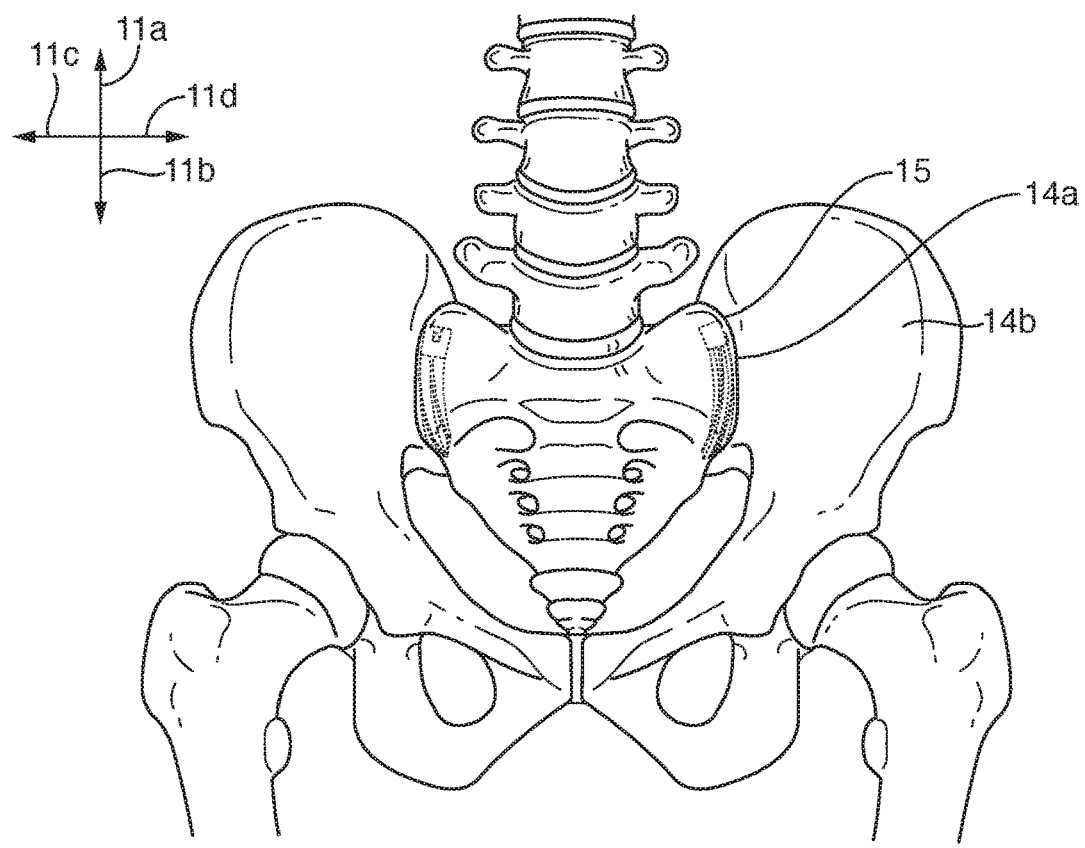
FIG. 1T is an anterior (front elevation) view thereof.
Figure 1U:
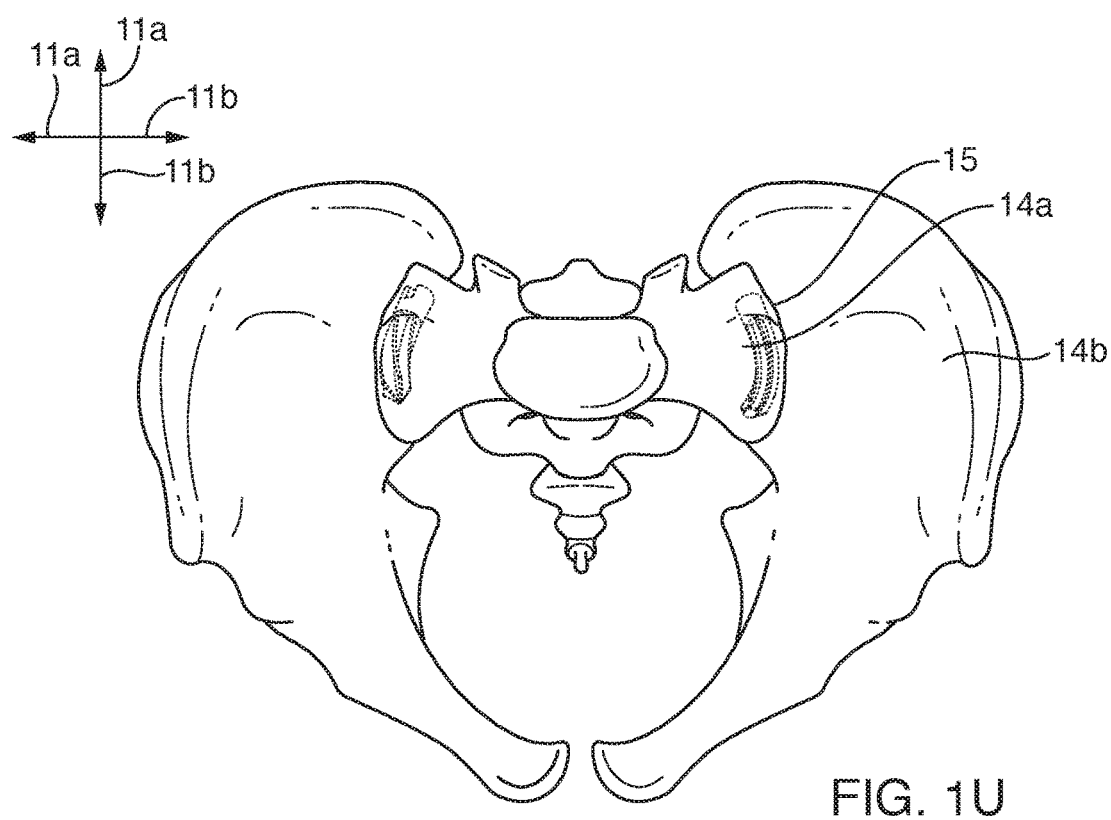
FIG. 1U is a superior (top plan) view thereof.
Figure 1V:
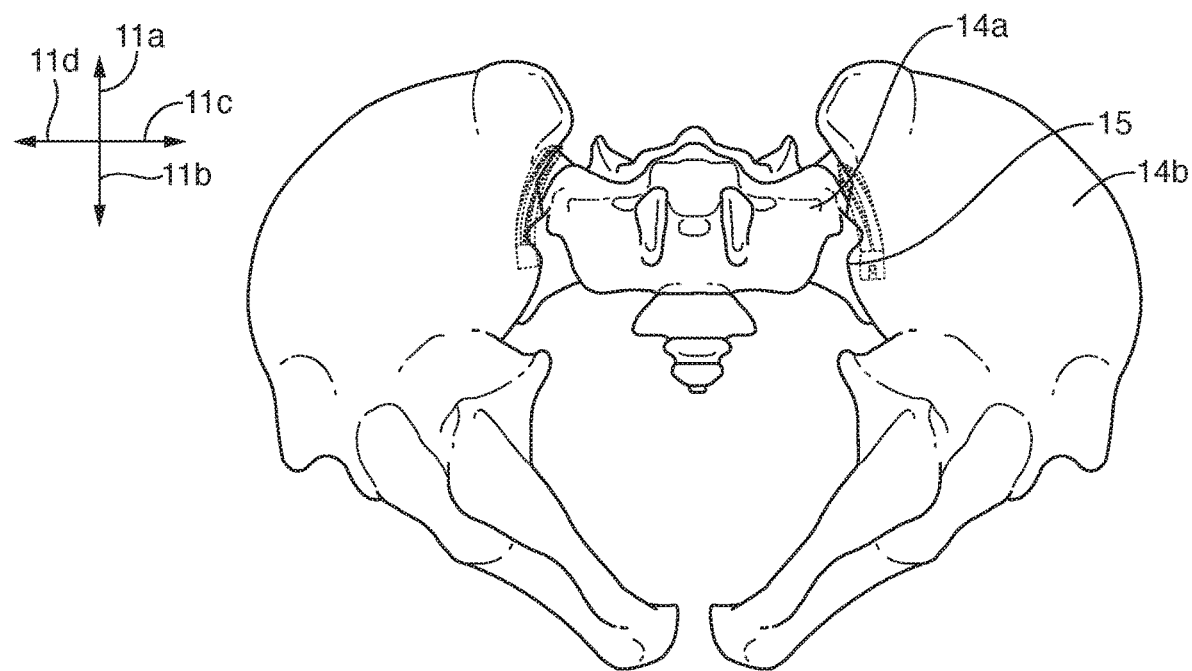
FIG. 1V is an inferior (bottom plan) view thereof.
Figure 1W:
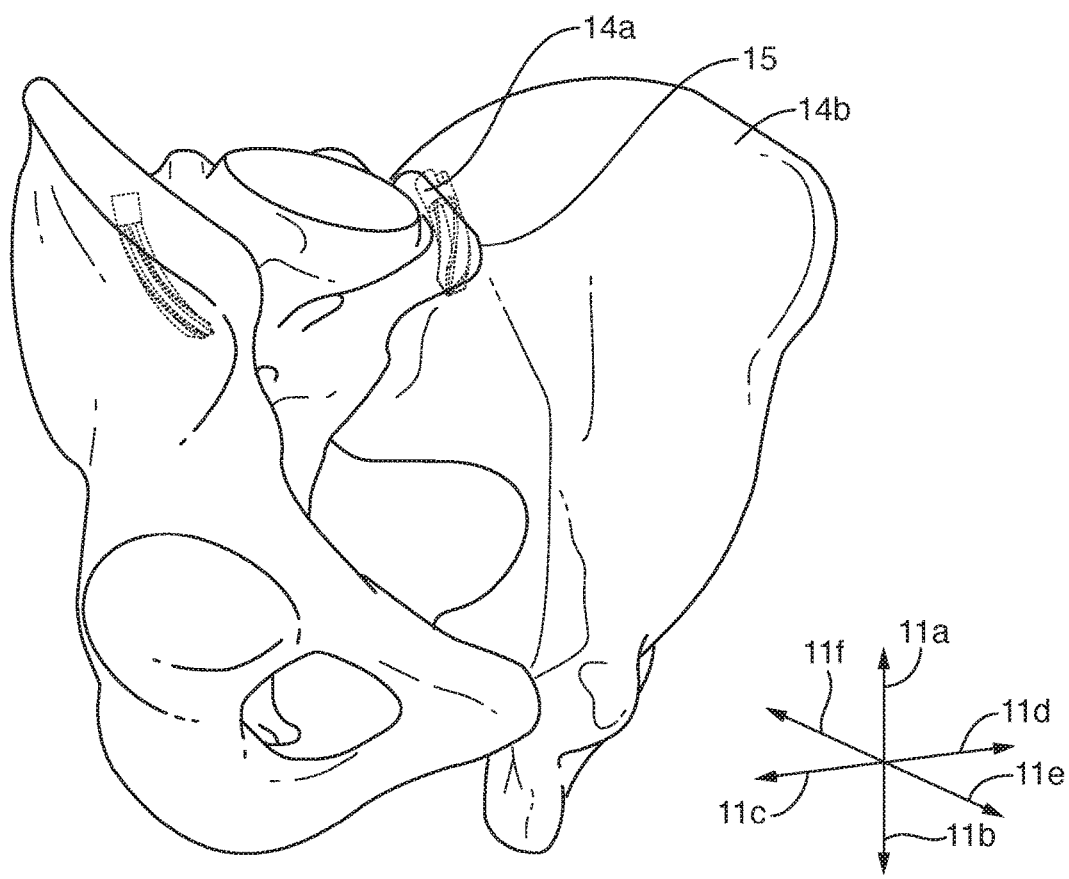
FIG. 1W is a superior and anterior (upper and frontal), perspective view thereof.

It will be readily understood that the components of the present invention, as generally described and illustrated in the drawings herein, may be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Figure 1X:
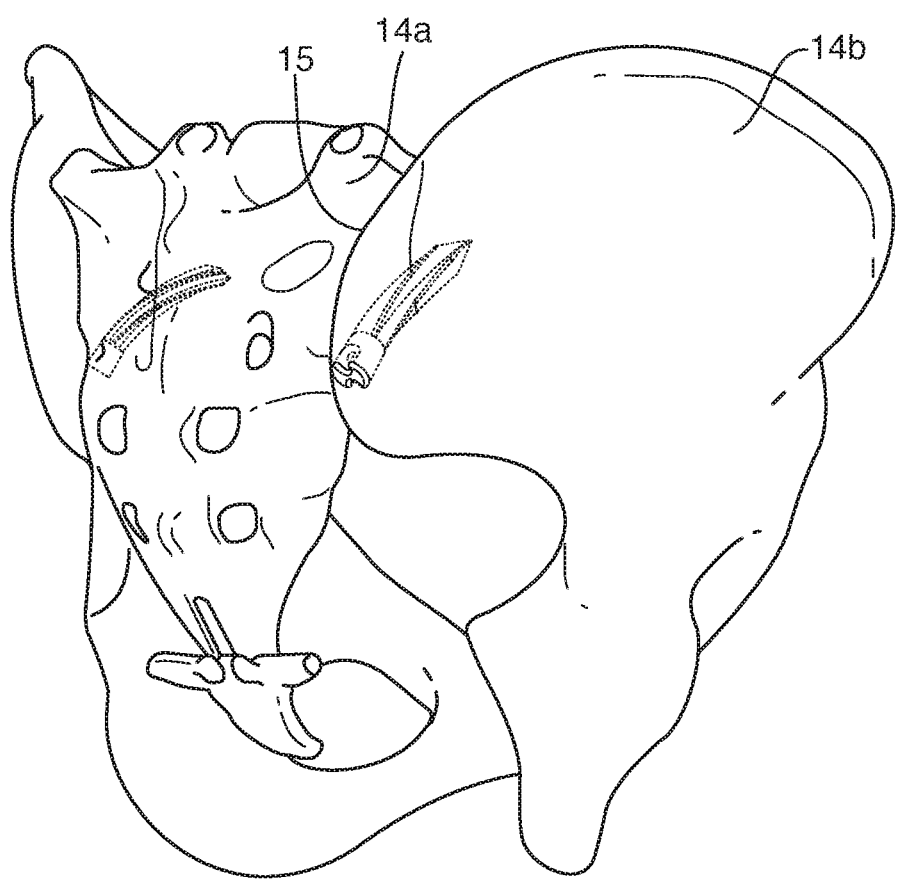
FIG. 1X is an inferior and posterior (lower and rear), perspective view thereof.
Figure 1X:
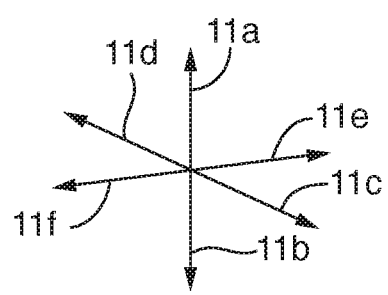
Figure 2A:
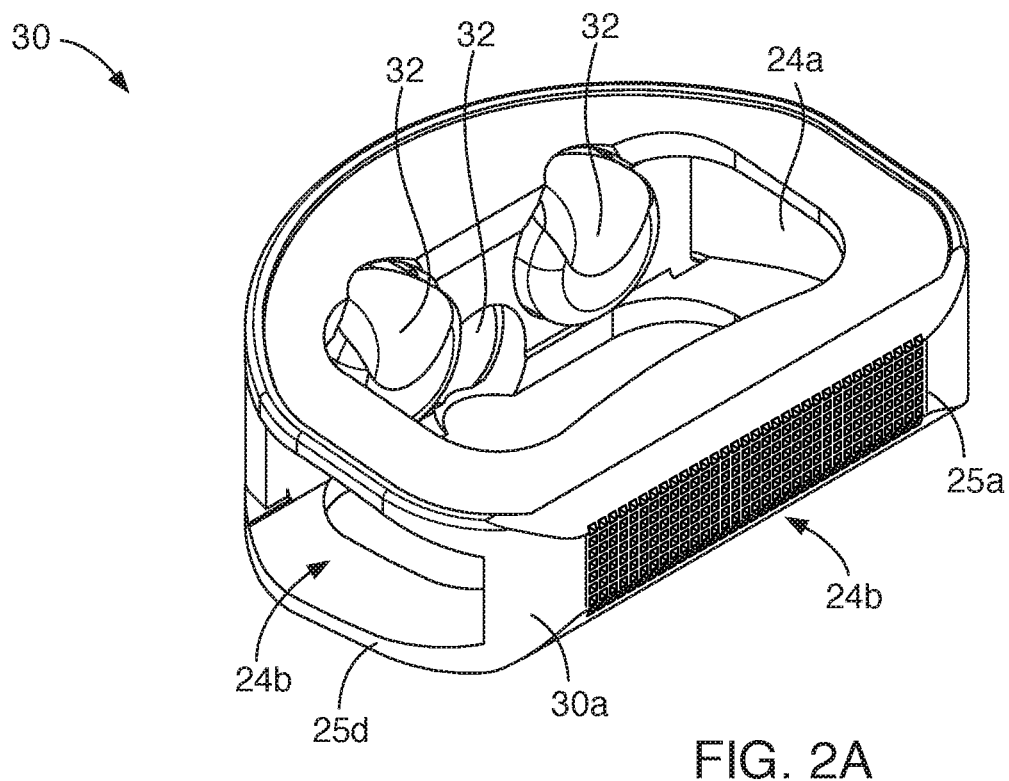
FIG. 2A is a superior and anterior (upper and frontal) perspective view of one embodiment of a frame operable as a spacer in certain embodiments of methods and apparatus in accordance with the invention.
Figure 2B:
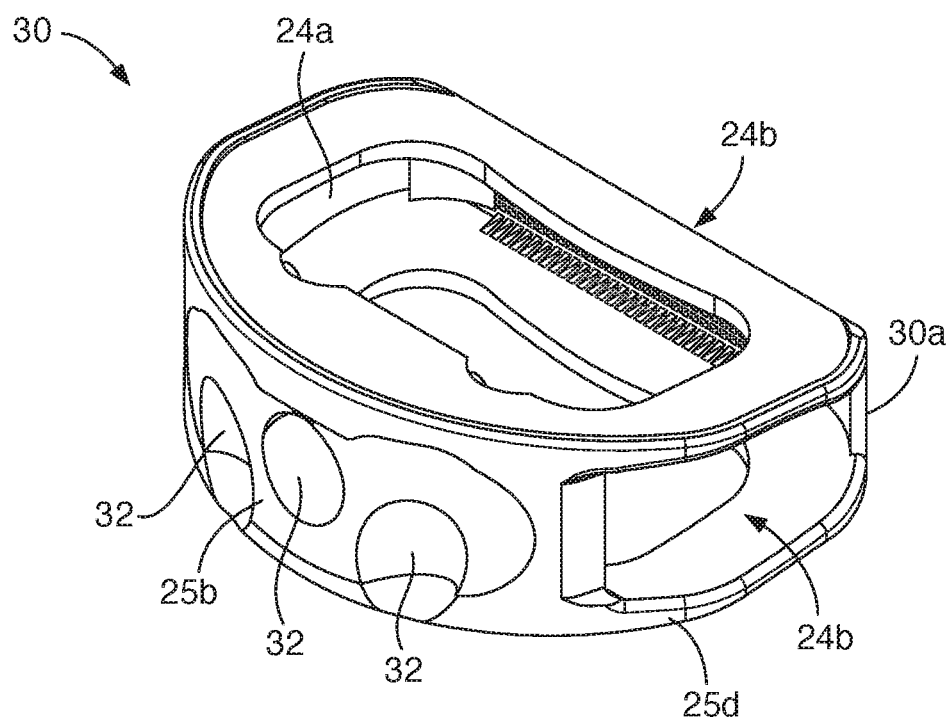
FIG. 2B is an inferior and posterior (lower and rear), perspective view thereof.
Figure 2C:
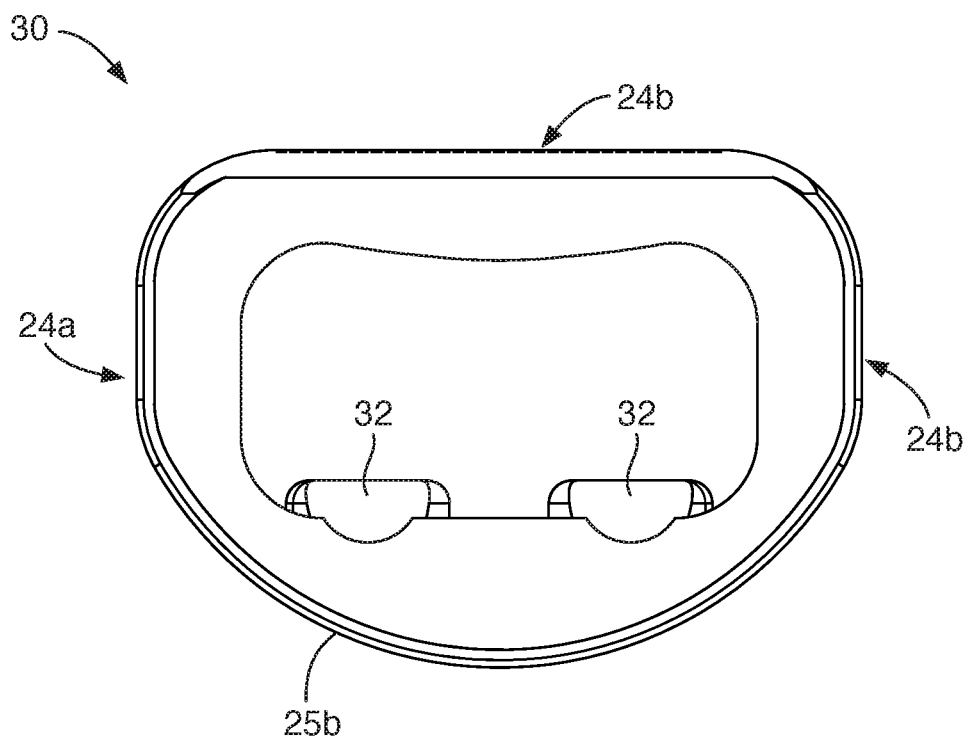
FIG. 2C is a superior (top plan) view thereof.
Figure 2D:
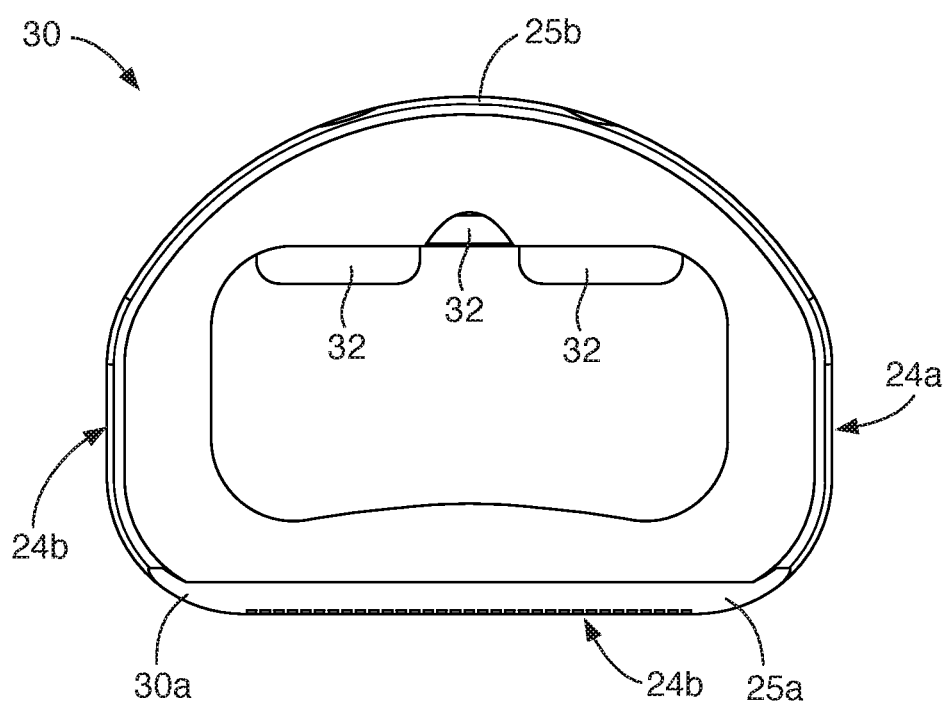
FIG. 2D is an inferior (bottom plan) view thereof.
Figure 2E:
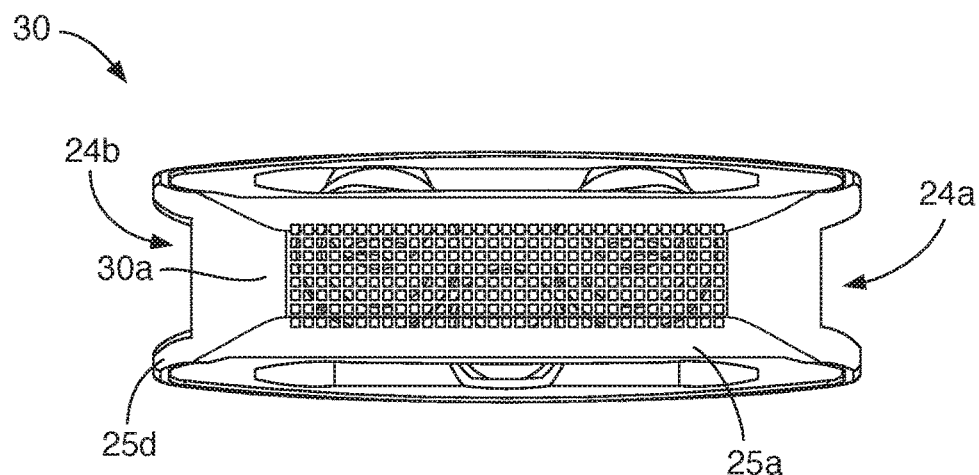
FIG. 2E is an anterior (front elevation) view thereof.
Figure 2F:
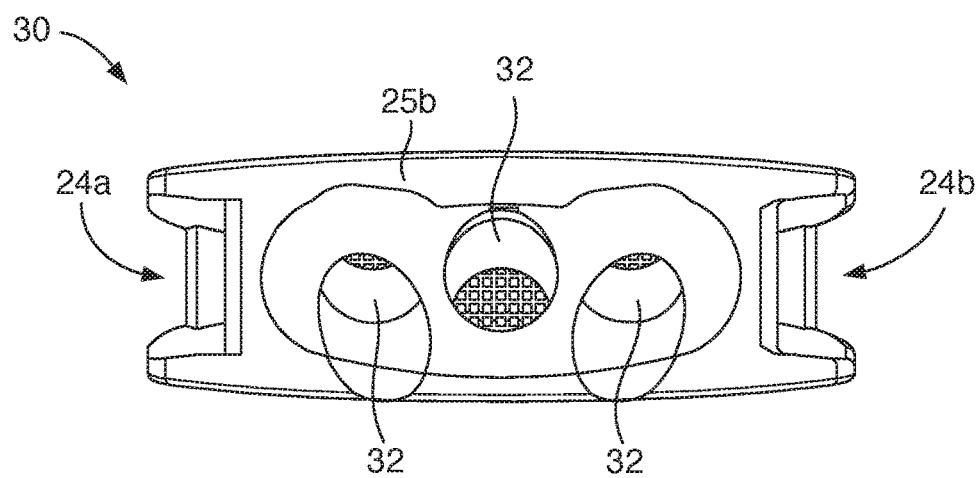
FIG. 2F is a posterior (rear elevation) view thereof.
Figure 2G:
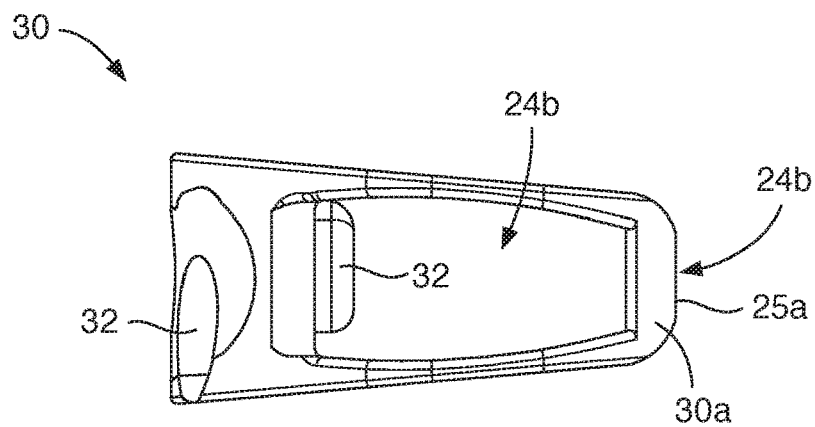
FIG. 2G is a lateral (side elevation) view thereof, an opposite side being a mirror image thereof.
Figure 3A:
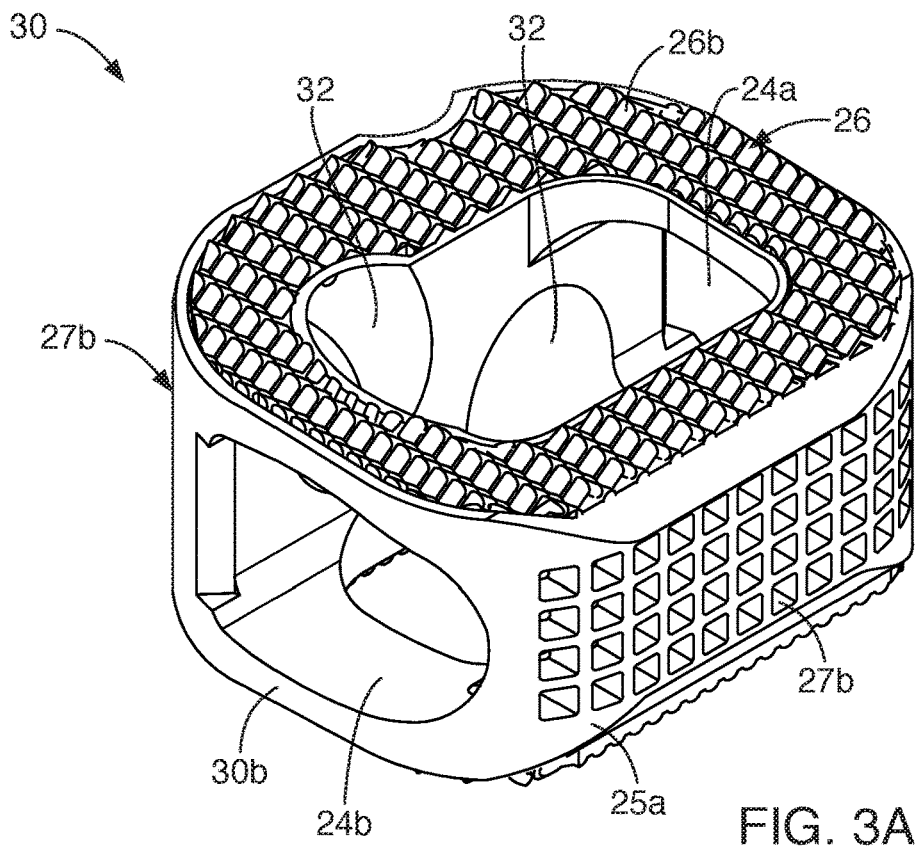
FIG. 3A is a superior, anterior perspective view of a heavily textured and porous frame operable as a spacer in accordance with the invention.
Figure 3B:
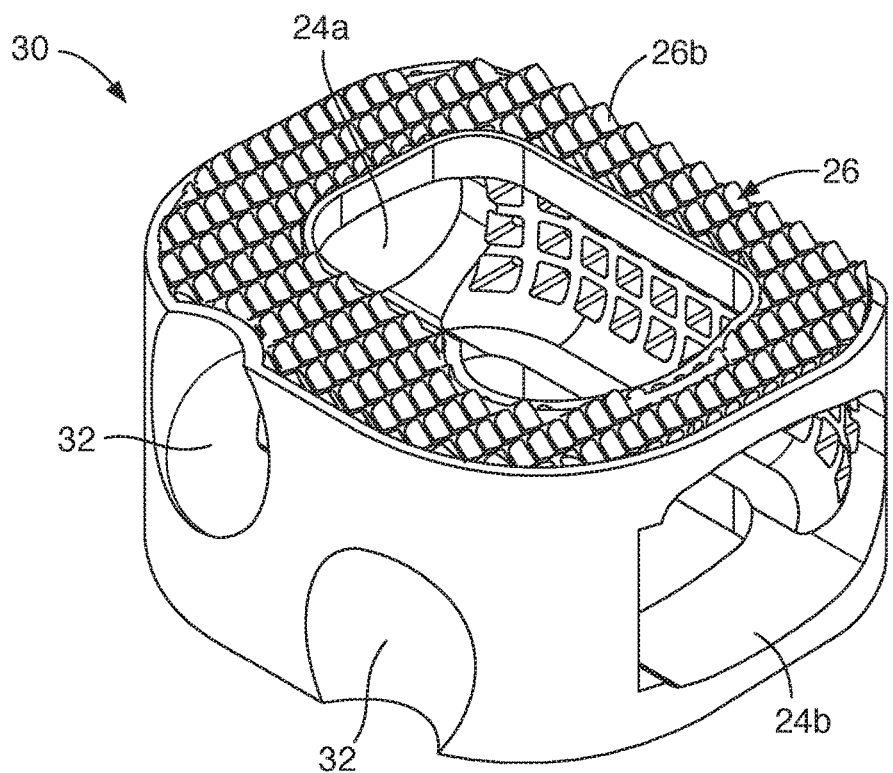
FIG. 3B is a posterior and inferior (lower and rear) perspective view thereof.
Figure 3C:
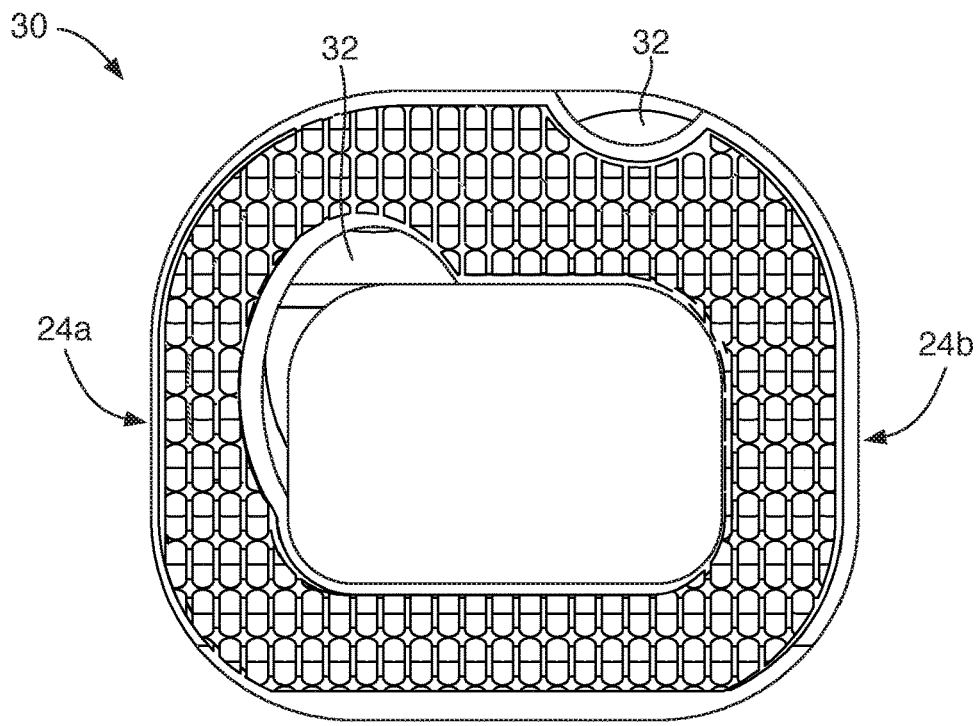
FIG. 3C is a superior (top plan) view thereof.
Figure 3D:
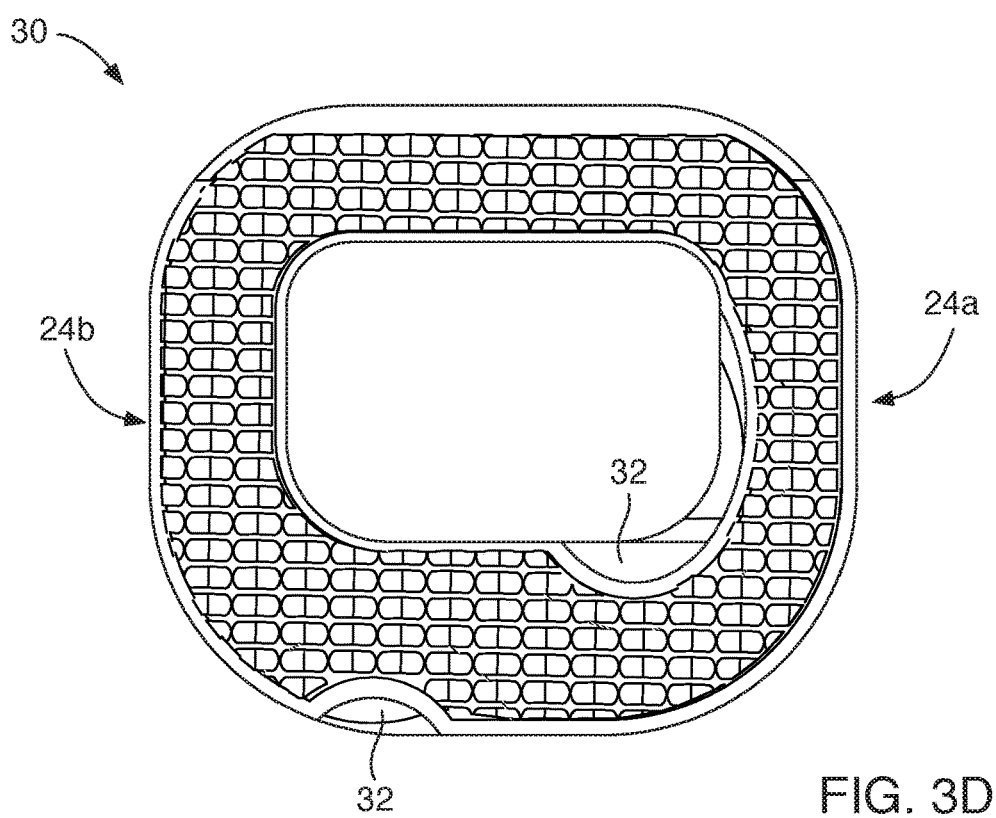
FIG. 3D is an inferior (bottom plan) view thereof.
Figure 3E:
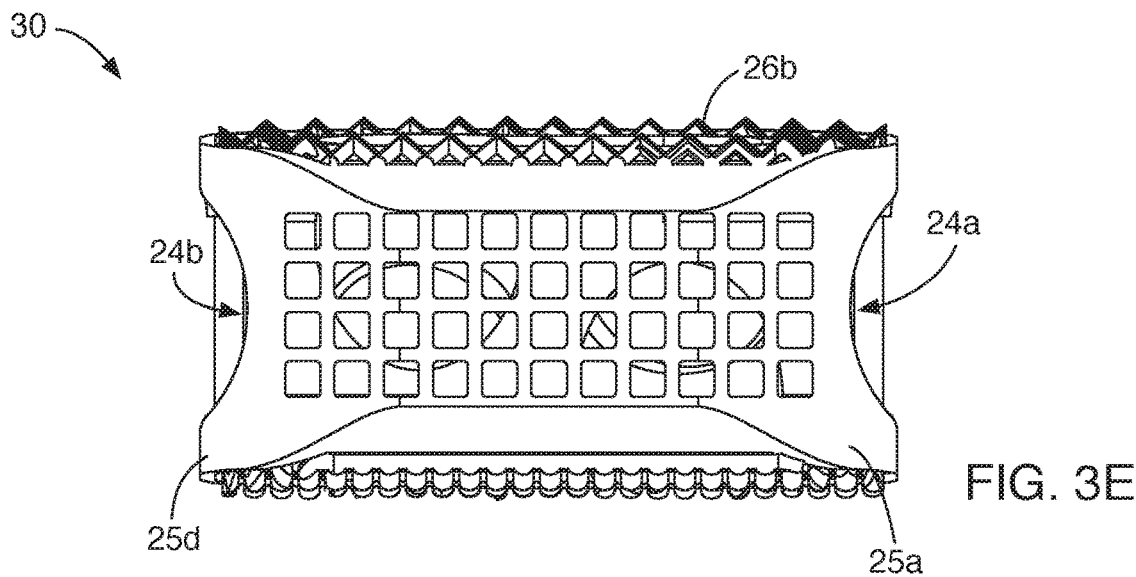
FIG. 3E is an anterior (front elevation) view thereof.
Figure 3F:
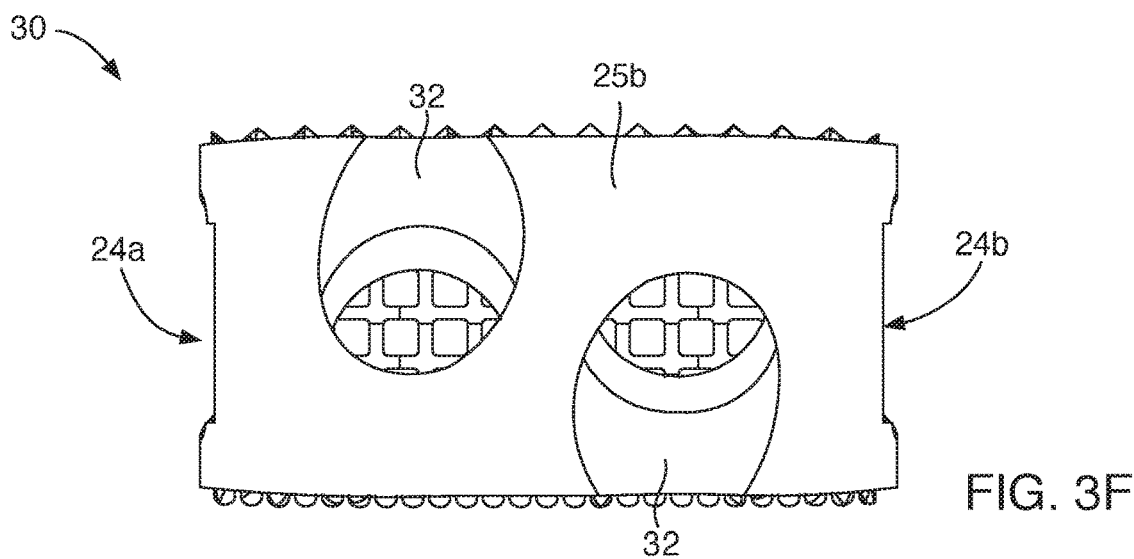
FIG. 3F is a posterior (rear elevation) view thereof.
Figure 3G:
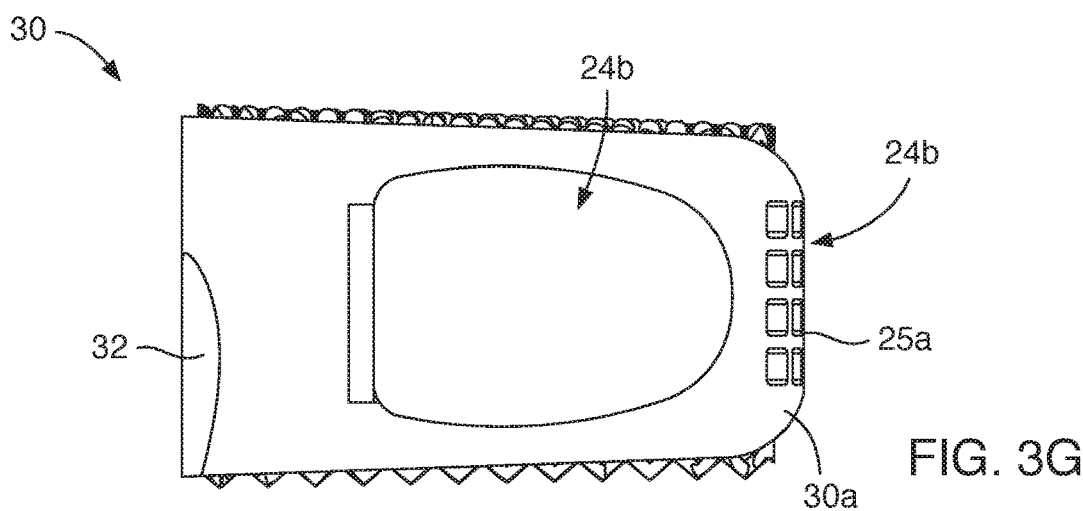
FIG. 3G is a lateral (side elevation) view thereof, an opposite side being a mirror image thereof.

Referring to FIGS. 1A through 1X, a system 10 in accordance with the invention may be used to anchor one bone or bone structure (fragment, bone, or the like) to another. Various embodiments are shown, grouped as FIGS. 1A through 1G directed to cross-joint anchoring by multiple anchors, FIGS. 1H through 1Q directed to cross-joint anchoring by a single anchor, and FIGS. 1R through 1X directed to anchoring by an implant (metallic anchor) within and along the direction of the sacro-Iliac (SI) joint requiring fixation by the presence of the implant.

Typically, the bones 14 may be defined by the body part to which they pertain. The body may be used to define directions 11 with respect thereto (e.g., a human or an animal, but typically a human). In the illustrated embodiment, the direction 11a is a vertical direction 11a, while a lateral direction 11b may be thought of as a left or right direction.

In medical parlance, lateral is an expression meaning toward the left or right side of a subject outward. Meanwhile, medial is used to mean toward a center plane or center of symmetry of a subject. Here, lateral and medial will be used as in medical technology. However, a lateral direction 11b will be either left or right without regard to whether it is traversing in a lateral direction, with respect to the subject, or a medial direction. Finally, a direction 11c covers any forward or backward (anterior or posterior) direction with respect to a subject. Thus, a direction 11c refers to that front and rear, forward and backward, direction. Nevertheless, without a reference number, anterior and posterior maintain their same medical meanings, as do lateral and medial, as well as superior (up) and inferior (down).

An anchor 12 may be used in multiples with or without a frame 30 (see FIGS. 2A through 4C). It may be of a pointed type 12a or of a hollow type 12b, also referred to as a cored type 12b. The helical splines 20 of the anchors 12, combined with an arcuate center line 17 (which is therefore not really a line 17 but a curve 17 or arc 17) are configured to twist and spiral along an axis not necessarily within the actual material of an anchor 12.

For example, in the illustrated embodiment, bones 14 are exemplified by a sacrum 14a and an ilium 14b. These bones 14 may be referred to generally as bones 14 or by the trailing letters as 14a, 14b, designating specific instances 14a, 14b of particular items within the classification or type, here identified by the number 14 for bones 14. Herein, a reference numeral will refer to a type or class of items, while that same reference numeral with a trailing letter refers to a particular instance or configuration thereof.

The bones 14a, 14b may meet at a joint 15 or interface 15. In the illustrated embodiment, that joint 15 is known as the sacroiliac joint 15. The joint 15 itself is actually formed of flexible, cartilaginous material. With age, deterioration, disease, inflammation, or the like, a particular joint 15 may become damaged, partially destroyed, and otherwise subject to excessive motion between the two individual bones 14a, 14b interfacing at the joint 15. Accordingly, a "fixation" (growing rigidly together) as that term is understood in orthopedic surgery, may be required. When the flexible joint 15 becomes too flexible, movement may cause abrasion and other damage between the bones 14a, 14b. They may be fused to rigidize and literally grow together across the joint 15. The joint 15 may be scraped to promote active bone healing and growth, and to remove ineffective cartilage and its debris remaining in the joint 15.

In a sacroiliac joint 15 as illustrated, anchors 12 may be inserted in a medial direction 11b through the ilium 14b into the sacrum 14a stopped only by the head 16 of the anchor 12 at the cortical type bone 14 near the outer surface of the bones 14a, 14b. A center line 17 of each anchor 12 is arcuate in shape. It may be or lie within a single plane, or may itself be helical in shape having a curvature circumferentially as well as radial along its length. Such an embodiment would reflect an extremely long pitch (several lengths of the anchor 12 per 360 degrees of revolution or progression of a spline 20 proceeding therealong and therearound). A very long-pitch, centerless screw may be thought of as a coil that does not necessarily have to include any actual matter along its center line, yet spirals about a central axis whether that axis is straight, curved, or helical.

Each anchor 12 regardless of its particular type 12a, 12b will typically have a point 18 or a leading edge 18, respectively. A pointed anchor 12a has all splines coming together to form a specific point 18. Meanwhile, a hollow (cored) anchor 12b, having a tubular shape inside the splines 20, thereby leaves a sharpened cutting edge 18 as a leading edge 18 to promote its progress through bone. A pilot hole may be drilled for starting an anchor 12 and will typically only extend a short distance (typically about three diameters). Inasmuch as the helical splines 20 extend away from the center line 17 (curve 17), each anchor 12 must rotate into position follow its point 18 or leading edge 18 and the path dictated by the splines 20.

The splines 20 extend radially, and progress axially as well as angling circumferentially about the center line 17 of an anchor 12. In the pointed embodiment 12a, virtually the entire anchor 12a is formed of splines 20 extending radially and axially from and along, respectively, the center line 17. In contrast, the hollow anchor 12b has splines extending away from a lumen 22 or channel 22 defined by a wall 23 spaced from and traversing along the arcuate center line 17. From that wall 23 around the lumen 22, the splines 20 extend radially. Splines 20 have at least one of three possible mechanisms (texture, porosity, apertures) for encouraging securement thereto by the surrounding bone material.

For example, the lumen 22 may actually be accessible by elongated, somewhat rounded, oblong apertures 60. For example, apertures 60a through the splines 20 may permit bone growth through individual splines 20. Likewise, apertures 60b through the wall 23 may permit bone growth inside and through the lumen 22 and connecting through those apertures 60b to bone growth between adjacent splines 20.

In addition, the splines 20, the wall 23, or both may be formed of a porous material (e.g., sintered metal) provided with a rough texture. Sintering provides particles of a metal that are partially melted at their interfaces in order to provide an atomic bond between adjacent particles, while still leaving small, often microscopic interstices therebetween. Accordingly, fluids, gases, and cellular structures inherent in bone 14 may actually grow into, through, or both such splines 60a or walls 60b, through the porosity itself as well as through possible apertures 60. Thus, one may think of a grow-through-aperture 60 (GTA 60) as a comparatively larger aperture 60, although a porosity of much smaller effective diameter (4×area÷perimeter) through the solid material itself may also exist.

The texturing on any given component such as a spline 20 or wall 23 may provide resistance against shear. That is, a texturing provides concavities and convexities at the surface itself of a solid, thereby resisting the physical shearing that might otherwise occur between a hard, slick, slippery, smooth, and non-bonded surface of a solid with respect to adjacent material of a bone 14.

Referring to FIGS. 2A through 4C, one will note various mechanisms to stabilize anchors 12. Anchors 12 in spinal surgeries often rely on spacers 30 or frames 30 providing apertures 24 as GTA 24 in vertical configurations 24a or horizontal configurations 24b.

Typically, walls 25 may proceed in any suitable direction, such as vertical walls 25a, horizontal walls 25b, and the like. Texturing 26 may be applied to any particular wall 25. For example, in the images of FIGS. 2A through 2G, corrugation constitute a form of texturing 26. On the other hand, a highly roughened texturing 26b is found in the embodiment of FIGS. 3A through 3G.

Each frame 20 may be characterized by various surfaces 27. Surfaces 27 may be inside or outside the open spaces within the frame 30. In the illustrated embodiments, a rear surface 27a may receive anchors 12, which will then pass into a vertically open GTA aperture 24a.

At the same time, a front surface 27b may be treated with texturing 26 or apertures 24g as GTA apertures 24g.

Typically, front surfaces 27b may be textured in any suitable way, including smoothly textured, as side surfaces 27c may actually be perforated. For example, manufacturing may require casting or molding in such a way that "core pulls" must be inserted and retracted in a mold while casting or otherwise forming a frame 30. Thus, side surfaces 27c may be comparatively smaller than front surfaces 27b, and particularly smaller in rear surfaces 27a that will tend to orient and secure anchors 12 passing therethrough.

Side surfaces 27c may be perforated or completely open between top surfaces 27d and bottom surfaces 27d, collectively referred to as horizontal surfaces 27d. Porous materials 28 may be used to texture any surfaces 27. They may also be used as the fundamental material from which an entire frame will be made. Sintering, for example, results in a porous material 28 forming the basic frame 30.

In the individual embodiments of FIGS. 2A through 2G, 3A through 3G, and 4A through 4C, the frame 30a has a corrugated horizontal surface 27d, and thus is considered a corrugated frame 30a. Meanwhile, the embodiment of FIGS. 3A through 3G is a heavily textured frame 30b. Meanwhile, the loop frame 30c is made up primarily of interconnected loops 34.

In general, apertures 32 may be formed as guides 32 for anchors 12 through frames 30. However, anchors 12 may be used by themselves. Typically, two bones 14a, 14b to be secured to one another (fixed, healed into one) will require at least two and often more anchors 12 extending therebetween. Anchors 12 in accordance with the invention provide compression at an intermediate joint 15 to be fused. Force is maintained by spiraling in a helical direction, thus spiraling the curved center line 17 or axis 17 of each anchor 12. Installation may include applying a certain amount of torque to encourage tracking (cutting and spiraling) along the splines 20.

Some functional apertures 32 include a left anchor aperture 32a, a right anchor aperture 32b, and a center anchor 32c. The single center anchor 32c may be replaced by inner anchors 32c paired between the left anchor 32a and the right anchor 32b. Meanwhile, a frame 30 in its back or posterior surface 27 may include a tool aperture 32e for receiving, engaging, anchoring, fixing, or the like a tool 32e. Meanwhile, GTA apertures 32f may abound wherever appropriate. For example, side apertures 24b may provide through-growth space or real estate within an individual frame 30.

Figure 4A:
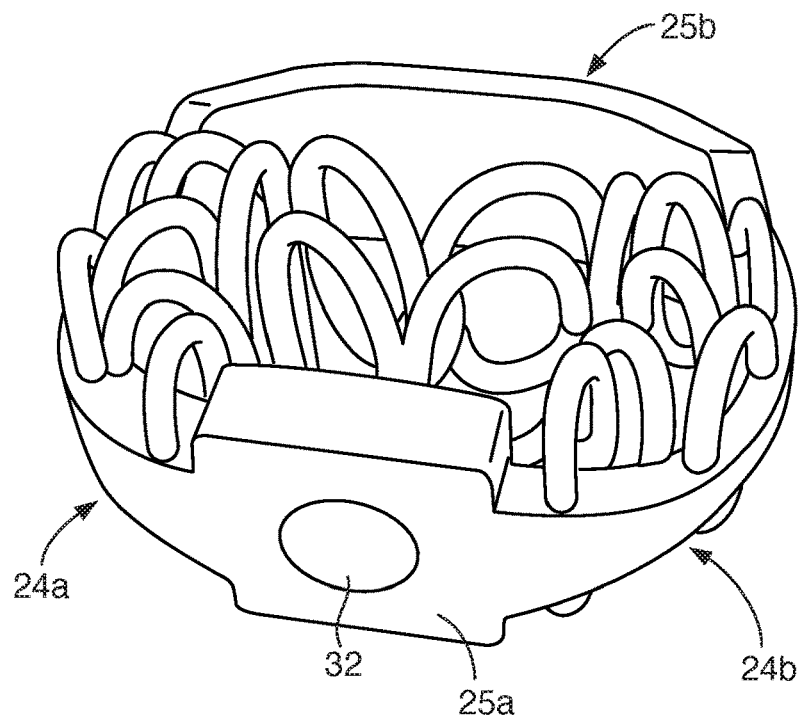
FIG. 4A is a superior and anterior (upper and frontal) perspective view of a frame operable as a spacer in accordance with the invention, having a looped, internal, structural configuration.
Figure 4B:
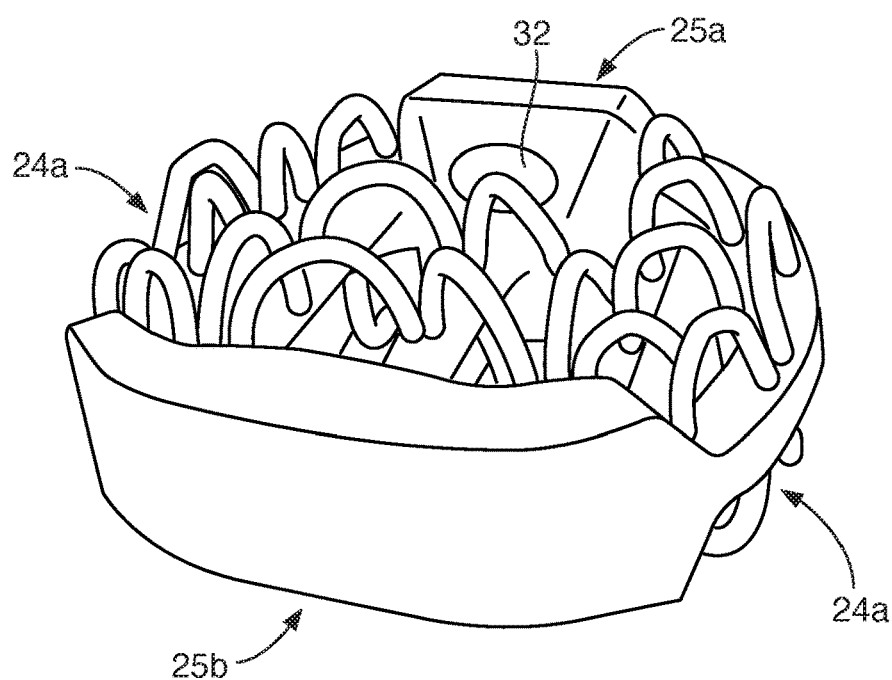
FIG. 4B is an inferior and posterior (lower and rear) perspective view thereof.
Figure 4C:
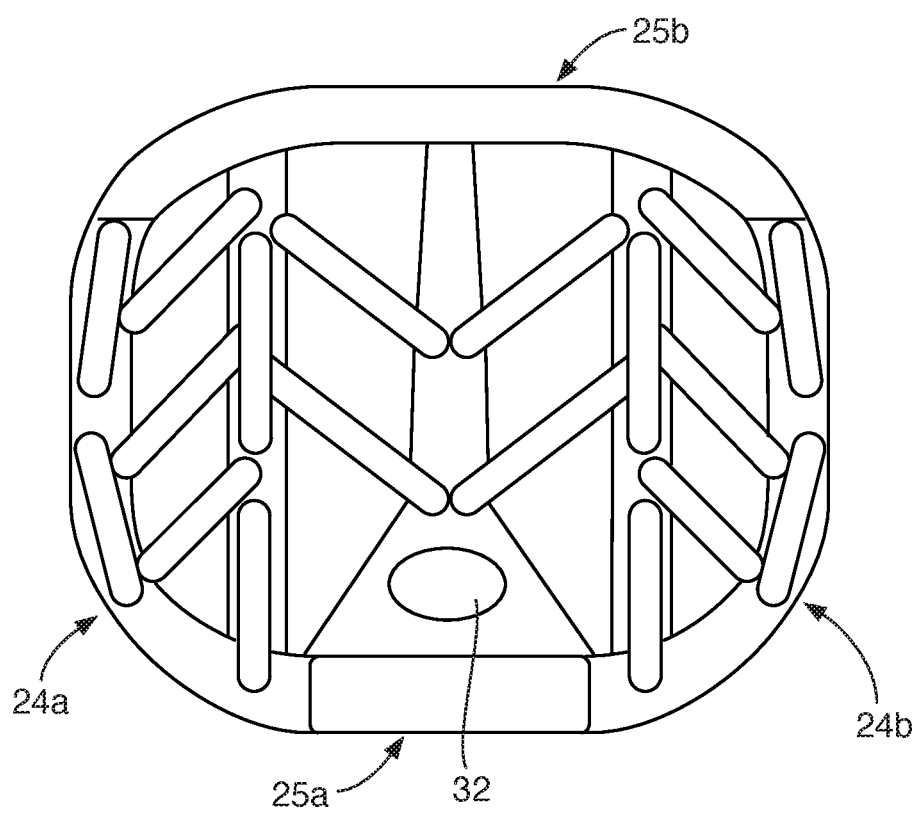
FIG. 4C is a superior (top plan) view thereof.

Referring to FIGS. 4A through 4C, a looped configuration 30c may include interconnected loops 34, formed by welding, casting, or the like. Loops 34 form a frame near a bottom surface, but otherwise barely fill a minority of the space between the walls 36. For example, a rear wall 36 has sufficient mass to stabilize anchors 12 passing therethrough. The front wall 36b need not have so much support. It may be necessary for the stability of adjacent bones 14 between which it may be lodged to promote growth therethrough.

The side walls 36c here are comparatively shallow. Meanwhile, the loops 34 may themselves provide support in a vertical direction 11a such as for joint filling, spinal spacing subsequent to disc removal, or the like. Through growth is usually contemplated between adjacent vertebrae or other bones joined across such a frame 30c. However, the comparatively larger diameter loops 34 (order of magnitude of a dimension of the frame 30) with their substantial gaps or apertures therethrough (order of magnitude of half the loop size). These loops 34 provide much space, and a more proportionate balance between the strength of bone and the frame strength that may be engineered to secure to bone or to promote through growth from one bone 14a to another 14b.

The proportions of the frames 30 are suitable for spinal surgery. For surgery in a degenerated sacroiliac joint 15, frame thickness may be considerably less (in the figures, the nominally vertical direction 11a). In comparison, other dimensions are larger in the lateral direction 11b and the fore and aft direction 11c. Thus, the rear apertures 32a, 32b, 32c may have much less space in which to fit, and less surface area available to guide an anchor 12 therethrough.

Nevertheless, a comparatively thin wall 36 such as a comparatively thin rear wall 36a corresponding to a comparatively flat or short (vertically 11a) frame 30 may nevertheless have a comparatively small thickness but sufficient to orient the head 16 of an anchor 12.

Typically, a frame 30 itself may provide a tie between adjacent bones 14. However, the anchors 12 are perfectly capable of passing through a first bone 14a and into a second bone 14b. Based on its angles, shear forces, and through growth, anchors 12 may be quickly secured to bone more firmly than conventional anchors and maintain compressive force. The concept of an arcuate spiral may improve tension in the anchor 12 and thus pull a joint into greater compression.

Referring to FIGS. 4A through 4C, one will note that a majority of the volume of the frame 30c is space. Due to the numerous loops 34 illustrated, the open volume in the frame 30c may be filled with bone fragments. The adjacent bones 14 on either side may be prepared to pursue growth by exposing "bleeding bone" at the outermost surface thereof. This encourages healing together and growth through the frame 30c. In certain embodiments, a comparatively thin but elongated frame 30 may be used to span a degenerated portion of a joint 15. This stabilization mechanism will support the growth or "through growth" of bone between any two adjacent bones 14a, 14b. The frame 30 may be placed to stabilize, orient, and position anchors 12, and to fill up any space removed or resorbed from the original bone 14 at the joint 15.

Figure 5:
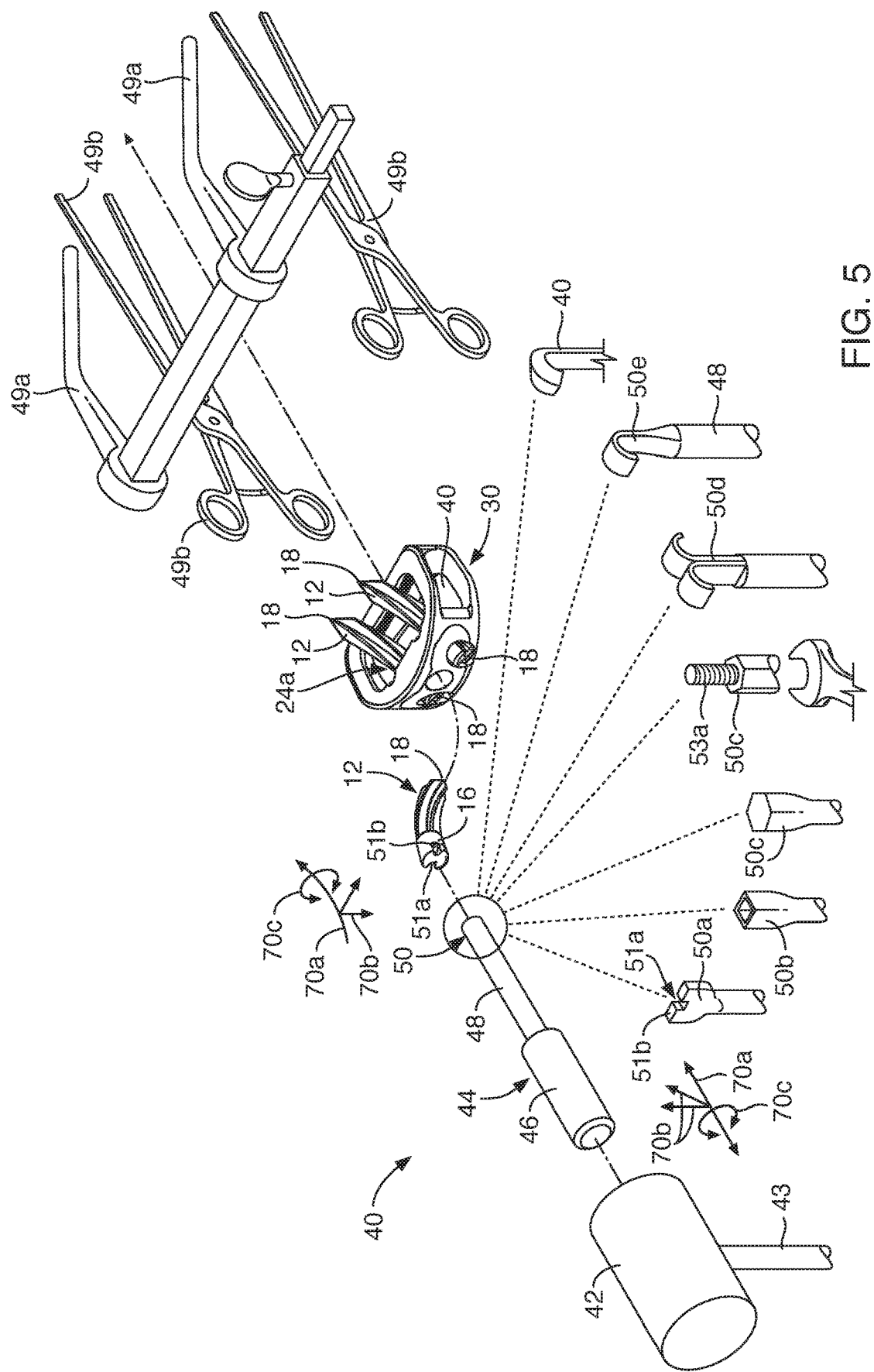
FIG. 5 is a perspective, exploded view of insertion tools, driving tools, anchors, optional frame, and distractors for installation of anchors.
Figure 6A:
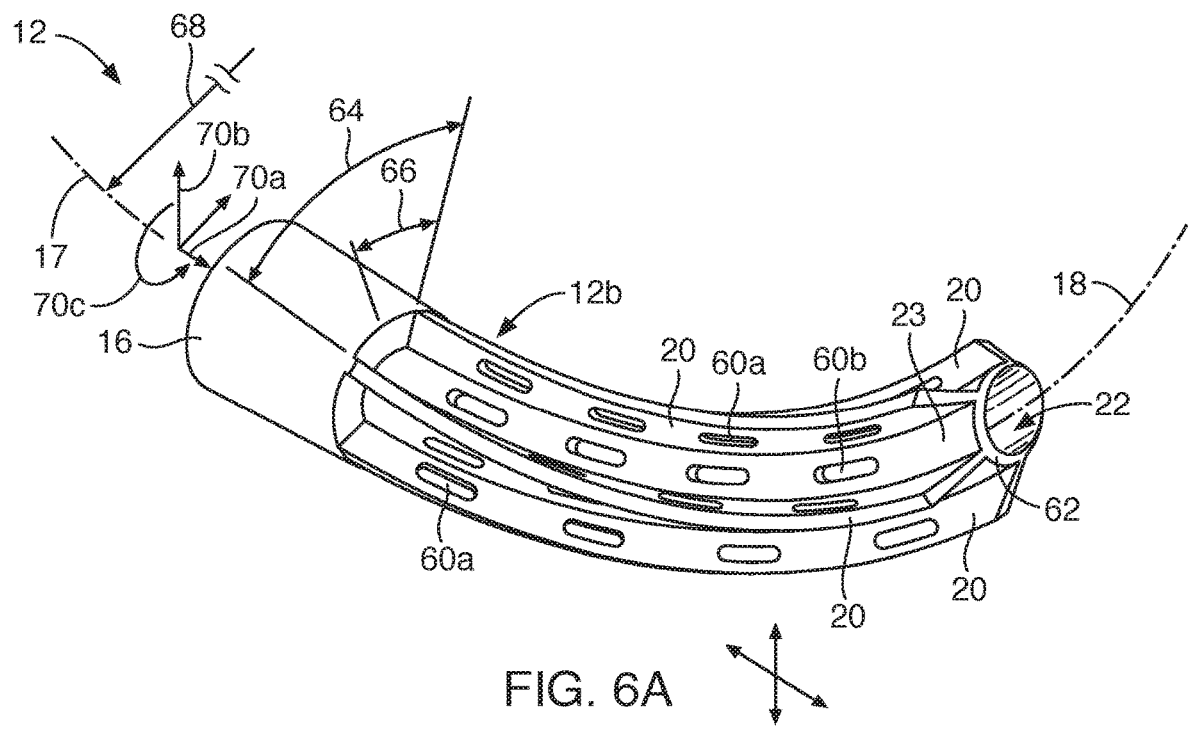
FIG. 6A is a perspective view of one embodiment of an anchor viewed from a distal end.
Figure 6B:
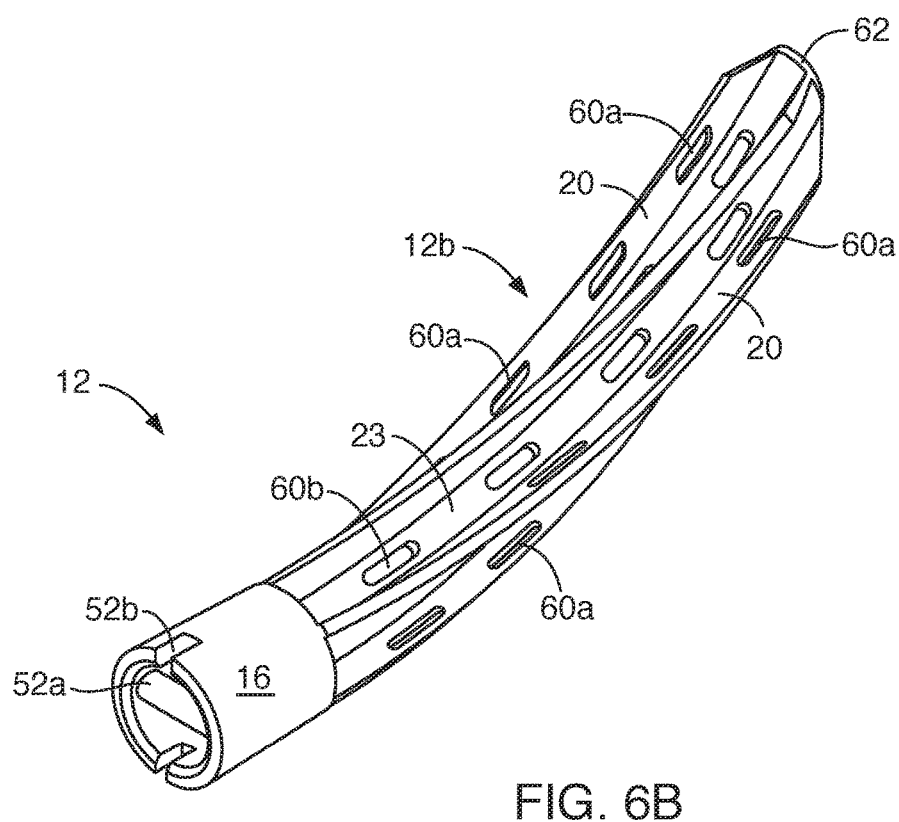
FIG. 6B is a perspective view from a proximal end of the cored type of splined anchor in one embodiment in accordance with the invention.
Figure 6C:
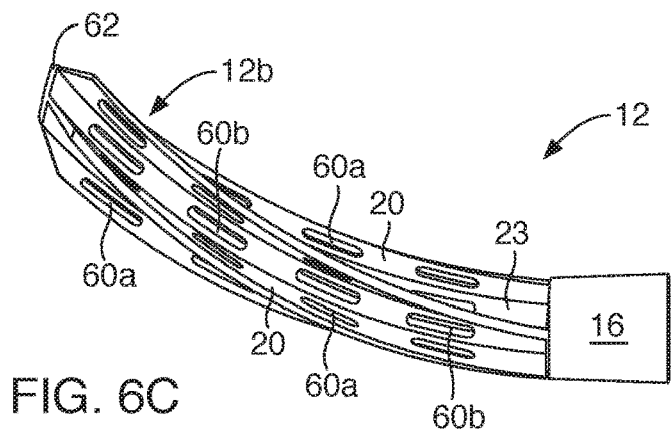
FIG. 6C is a proximal end view thereof.
Figure 6D:
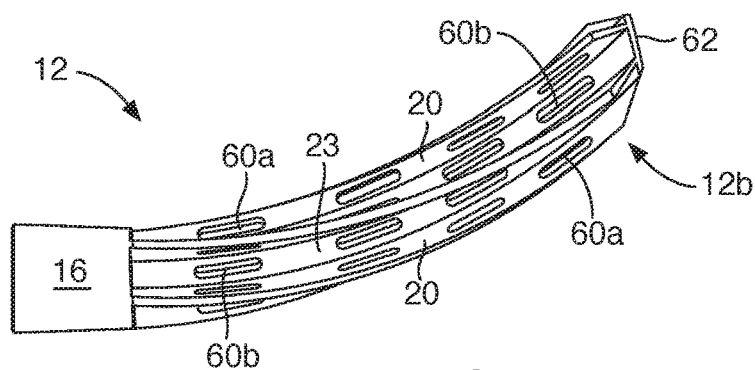
FIG. 6D is a distal end view thereof.
Figure 6E:
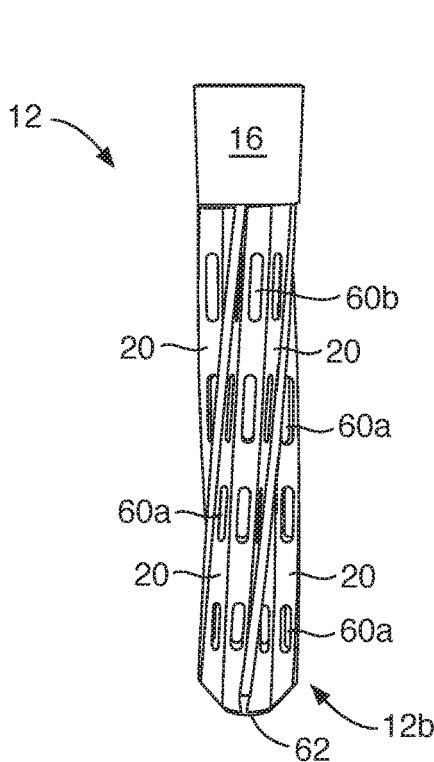
FIG. 6E is a side elevation view taken in a plane resulting in a straight envelope (outer boundary) and center curve.
Figure 6F:
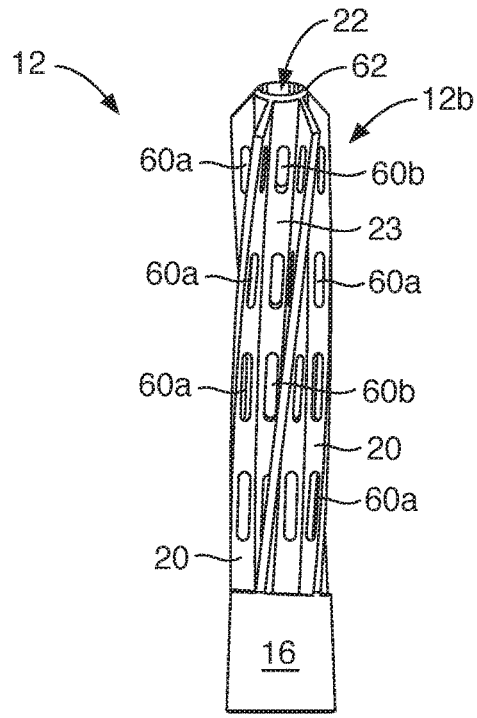
FIG. 6F is a side elevation view thereof taken in the plane in which the anchor central axis lies within a plane containing the curve.
Figures 6G, 6H:
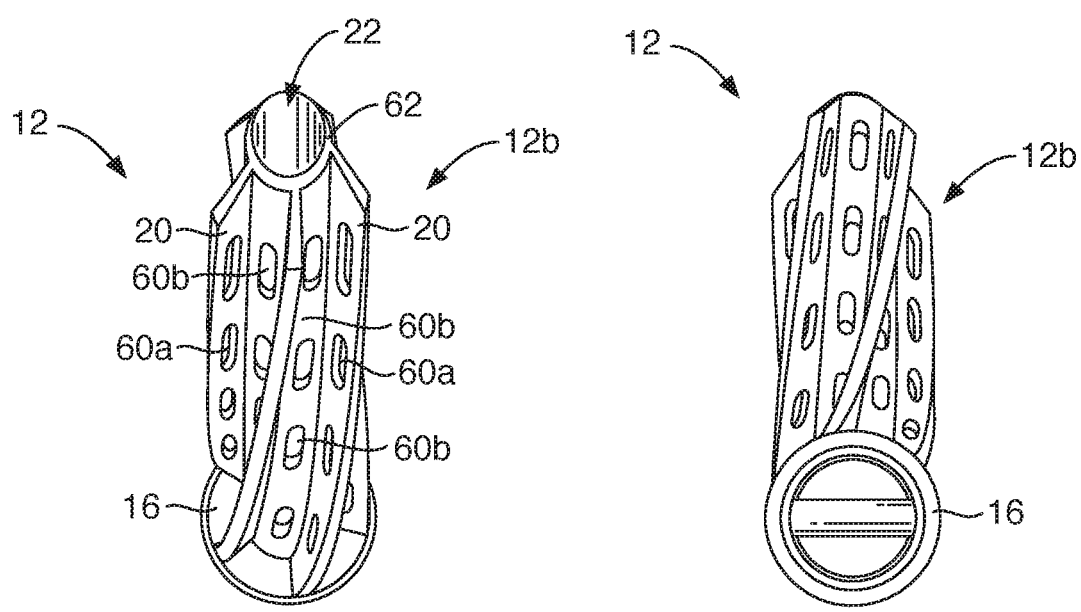
FIG. 6G is a cross-sectional view along a central axis near a distal end thereof.
FIG. 6H is a cross-sectional, end view thereof near a proximal end thereof.

Referring to FIG. 5, while continuing to refer generally to FIGS. 1A through 7G, an apparatus 40 and method 40 are illustrated. That is, one may think of the illustration of FIG. 5 as representing both a method 40 of insertion and retraction as well as a set of hardware 40 for so doing.

A surgeon may use a mallet 42 to drive an anchor 12 into bone 14 with or without a frame 30. The mallet 42 provides an impact loading (momentum, impulse, time and force). Impact is a comparatively short event. The mallet 42 transfers momentum of its motion and mass into a handle 46, a cutting edge 18 or leading edge 18, such as a point 18. It will cut into both cortical bone and cancellous bone, subject to circumferential loading on the surfaces of the splines 20.

Momentum is mass times velocity. Impulse is force through time. Energy is one half of a mass times the square of velocity. The mallet 42 transfers energy and momentum into the handle 46 upon striking. The handle 43 is held by a surgeon to position and optionally to provide a certain rotational (circumferential) force on the handle 46. The tool 44 will typically be rigidly secure between the handle 46 and shaft 48. The shaft 48 extends from inside the handle 46 to a point 50 that operates as an interface 50 with the head 16 of the anchor 12. The splines 20 are oriented to pass circumferentially 70c simultaneously. They present a much larger surface area (the sides or surfaces of the splines 20). That spline surface area will tend to urge the point 18 (regardless of whether actually pointed or hollow in the direction of the helical path of the splines 20.

The front edge of each spline 20 must effectively cut through bone, but presents comparatively much less surface area. Accordingly, even cancellous bone will tend to rotate the anchor 12 by moving the splines 20 circumferentially as they move axially along their direction of travel.

A surgeon may apply a moderate force in a circumferential direction 70c around the handle 46, in the same direction that the splines 20 angle or drift as they progress from the head 16 toward the point 18. This will assist the local bone that may otherwise tend to absorb more momentum from the splines 20 in rotating the splines 20 moving along their trajectory.

Urging circumferential 70c rotation of the handle 46 is not required, but may result in less trauma to the bone 14 responsible to provide circumferential force rotating the anchor 12 along its path. Of course, the point 18, terminating at the end of the arc that represents the center line 17 (center curve 17) through the anchor 12, will tend to arc along that path. Whether circular or spiral in and of itself, the path is followed by the splines 20. Possible rotational 70c urging of the handle 46 by a surgeon may help.

Again, the frame 30 may be used or not. In certain embodiments, the distractors 49a, 49b may be used to move tendon, muscles, or other tissue layers from an area into which a frame 30 is to be placed. Distractors are well known in the surgical art and need not be described in detail here. Suffice it to say that they operate in an opposite direction from forceps to spread tissues apart clearing space for a procedure to take place. Such a procedure inserting a frame 30 past tissues into a joint 15 between bones 14. Thus, the illustration of FIG. 5 shows various options, not all of which would be extant in a particular procedure.

The points 50 or interfaces 50 may be made in various configurations. For example, the point 50a has a slot 51a for receiving a crossbar 52 flanked on each side by a key 51b (slot 51a, key 51b, crossbar 52a, and the relief 52b in the illustrated embodiment of a head 16). For installation or insertion of an anchor 12, the point 50a may be suitable. In other embodiments, a square point 50b may be used to fit into the head 16. Alternatively, a hexagonal or other commercially available point 50c may be relied upon. The function of each of the heads 50 is to apply the impact load from the mallet 42 through the tool 44 and into anchor 12 along its axial direction 70a and, optionally apply a slight torque circumferentially 70c.

The engagement by a key 51b in a key way 52b or relief 52b may engage to provide a certain circumferential 70c torque. Torque is a force at a distance and therefore has units of force times distance. Axial force plus torque are suitable for progressing the anchor 12 both axially 70a along the arc of the center line 17 (center curve 17) and circumferentially 70c along the helical path described by the splines 20.

The points 50d, 50e may be used for insertion, but may provide additional features including a threaded stud 53a and a hook 53b. The threaded stub 53a may actually rotate with respect to the hexagonal point 50c in the device 50d, thereby permitting engagement of the female thread inside the head 16, for extraction. The hexagonal head 50c may penetrate into the head 16, after which turning a knurled handle, a T-handle, or another mechanism allows the threaded stud 53a to advance forward with respect thereto out of the hexagonal head 50c.

The hexagonal head 50c provides secure engagement for rotation in a circumferential direction 70c. The threaded stud 53a provides secure axial 70a engagement with the head 16 in order to draw back along the center line 17 (center curve 17). The handle 46 may be rotated in an opposite circumferential direction 70c from that of insertion. Accordingly, the anchor 12 may be removed by pulling and rotating. This will be on the same trajectory on which it passes into bone 14 to which it anchors. The significance of the threaded stud 53a and the hook 53b is that axial tension is not needed during the insertion process. Insertion needs only force or impact applied in an axial direction 70a, although some torque may assist.

Removal or loosening of the anchor 12 by the bone 14 does not occur readily because the axis 17 is curved not straight and the splines 20 are not aligned with it. That curve 17 has been modified in a helical path driven or guided by the splines 20. Accordingly, a force near the head 16 trying to force apart adjacent bones 14a, 14b is resisted by every spline 20 at its angle. That angle is not aligned with the axial direction 70a at the head 16 itself. Rather, along the entire length of the splines 20 the direction of force is continually changing. The orientation of each spline 20 surface changes along its entire length to secure the splines 20 and thereby the entire anchor 12 in bone 14, even cancellous bone. One will note that due to the extra long (multiple anchor 12 lengths) as a pitch, the mallet 42 and tool 44 may drive the anchor 12 into the bone 14. After that, the splines 20 provide a comparatively large surface area engaged at a comparatively modest force exactly the opposite effect as a conventional screw which tends to shear any cancellous bone into which it is anchored.

In fact, many conventional screws operate more like a sheet metal screw. A sheet metal screw passes through a single thin layer that is typically considerably less than one inch in thickness. One pitch is the difference in length between the crest of one thread and an adjacent thread. Not only do the splines 20 in accordance with the invention put less pressure on the cancellous bone, that pressure is distributed over a substantially larger area. There is not a location where the shear of a few threads can accumulate in close proximity to one another and at the exact same diameter as one another, in that nearly the same axially 70*a* location can be pulled through cancellous bones. Thus the coring out by simply stripping the threads cut into the cancellous bone is avoided.

Similarly, the hook type point 50*e*, similarly to the stud type point 50*d*, may engage the head 16, this time by a crossbar 52*a*. Meanwhile, the shaft 48 fits into the head 16 of the anchor 12. For example, the hook point 54*b* may pass into the head 16, pass the crossbar 52*a*, then may be drawn backward in the axial direction 70*a*. It may thus engage the crossbar 52*a* to urge rotation in a circumferential direction 70*c*, as well as drawing backward in an axial direction 70*a*.

Referring to FIGS. 6A through 6G, as well as FIGS. 7A through 7G, an anchor 12 in accordance with the invention may have a pointed configuration 12*a* or a hollow (cored or coring) configuration 12*b*. In the illustrated embodiments, one will see that the proximal end is formed into a head 16 for engaging a tool 44 for insertion or installation.

The tool 44 may have any of the engagement mechanisms 50*a* through 50*e* for driving, drawing, or both against the head 16. It may urge the point 18 or cutting edge 18 axially along the center curve 17 or center line 17. Progress along the center curve 17 necessarily drives the distal end of the anchor 12 at the leading edge 18 or cutting edge 18 (also called the point 18) along the axial direction 70*a*, where directions 70 are all with respect to the axis 17 or center line 17 through the anchor 12 along a curve 17.

Like the frames 30, the anchors 12 may be formed of a sintered material providing a porosity that can be penetrated in a straightforward manner by cellular material within a bone 14. Following insertion of the anchor 12, with the leading edge 18 or point 18 advancing first into the bone, and typically terminating when the head 16 abuts the cortical bone 14 or as shoulder countersunk therein. That is, the head 16 may be countersunk into cortical bone 14. There is substantial benefit to leaving the head 16 outside the cortical bone 14 material in order that the splines 20 may be stabilized by the cortical bone 14, and so that the head 16 may secure one portion of bone 14 to another.

To that end, a grow-through-aperture 60 or GTA 60 may be provided in any suitable portion of an anchor 12. For example, in the illustrated embodiments, a GTA 60*a* provides an opening 60*a* through a spline 20. It may be dressed or shaped to promote engagement with bone growth therethrough. Similarly, the wall 23 of the spline 20, surrounding the lumen 22 or channel 22, may likewise be perforated with GTA's 60*b* at some suitable length and width, spaced apart at an effective, intermediate spacing therebetween.

One will note that the helical trajectory of an anchor 12 upon entry into bone 14 is guided by the splines 20, which may in turn be guided or not by apertures 32 in the posterior wall 36*a* of a frame 30. Regardless, a suitable amount of urging in a circumferential direction 70*c* while driving or malleting an anchor 12 into place, the point 18 and splines 20 will move the distal end in accordance with the forces applied in a circumferential direction 70*c* by the splines 20 themselves. Thus, a combination of the splines 20 moving against already penetrated cancellous bone 14, as well as the outer cortical bone 14, will urge the rotation about the center curve 17, even as the arcuate shape of that center curve 17 within the anchor 12 imposes its own arcuate direction on those helical splines 20. That is, moving forward, the arcuate shape of the center curve 17 and consequently the anchor 12 will tend to move in an arc from a point of insertion. Meanwhile, the splines 20 and optional urging on the handle 46 in a circumferential direction 70*c* will also move that point 18 on a helical path combining the arcuate shape along the center curve 17, and helical shape (and resulting orientation) of the several splines 20.

To a certain extent, the angle 64 between adjacent splines 20 may be selected according to engineering principles. Likewise, the overall radial 70*b* dimension or height in a radial direction 70*b* of each spline 20 may be balanced against the diameter across the lumen 22. For example, the embodiment of FIGS. 7A through 7G, has no lumen 22. However, in certain embodiments, a comparatively large fraction of the overall dimension across an anchor 12 in a radial direction 70*b* may be balanced between the diameter of the lumen wall 23, against the altitude or radial 70*b* extension of those splines 20 away from that lumen wall 23.

In practice, the curvature of the path of leading edge 18 or point 18 is a combination of the center line 17 or center curve 17 and the helical disposition of the splines 20. This results in the adjacent bones 14*a*, 14*b* across a joint 15 being held firmly. The force direction across the joint (perpendicular to) a plane of the joint 15 is almost never aligned with the majority of area of the splines 20, especially following installation.

Figure 7A:
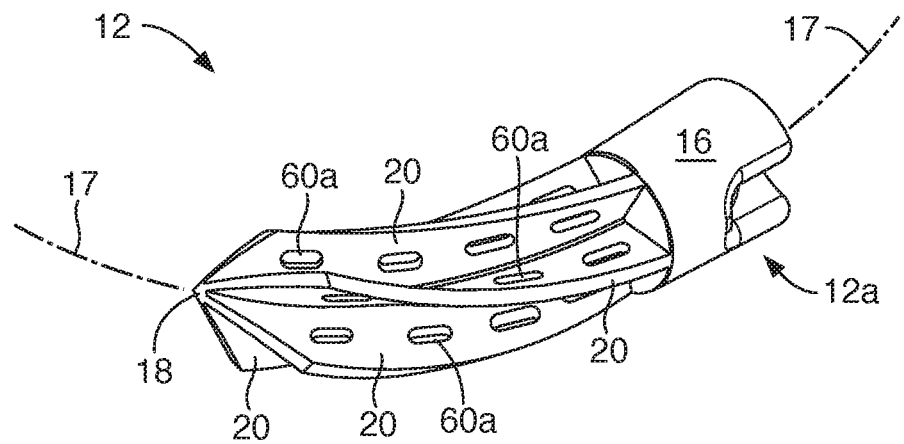
FIG. 7A is a perspective view from a distal end of an alternative embodiment of an anchor in accordance with the invention.
Figure 7B:
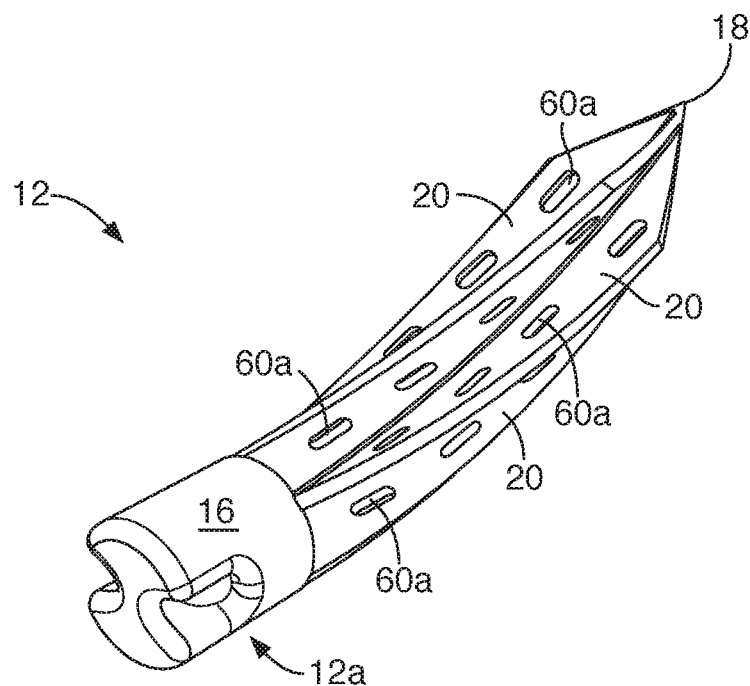
FIG. 7B is a perspective view from a proximal end thereof.
Figure 7C:
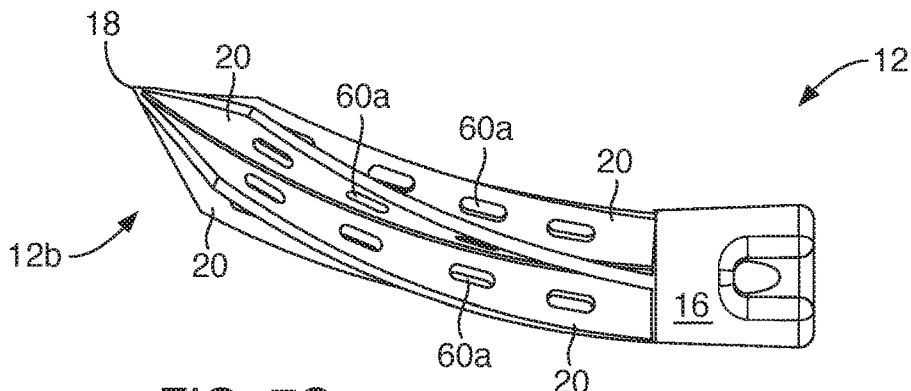
FIG. 7C is an end view thereof from a distal end.
Figure 7D:
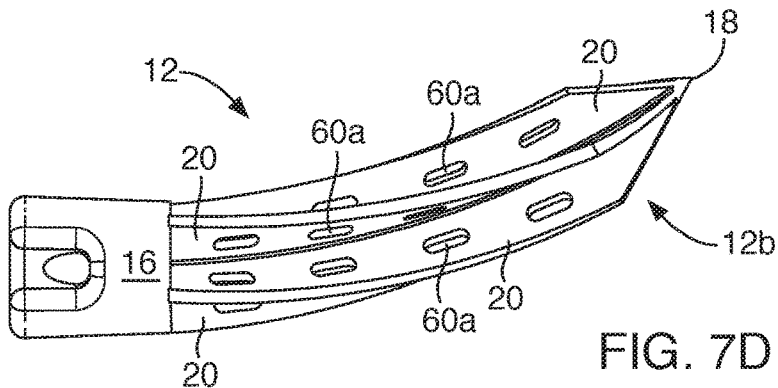
FIG. 7D is an end view thereof from a proximal end.
Figure 7E:
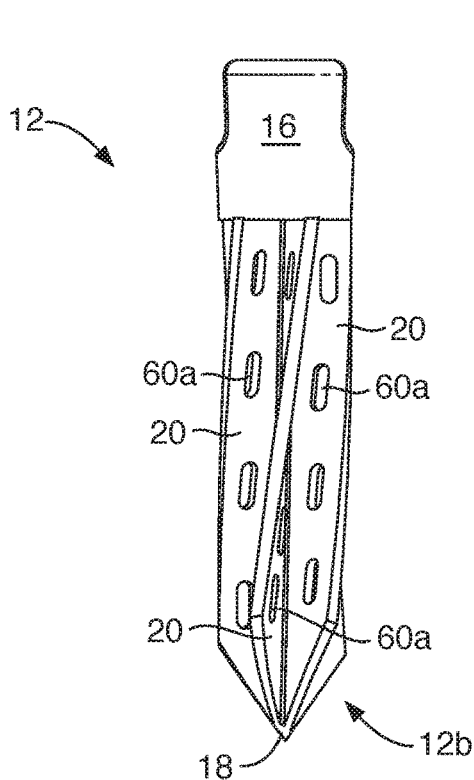
FIG. 7E is a side elevation view taken in a plane containing the curvature of the curved central axis through the anchor.
Figure 7F:
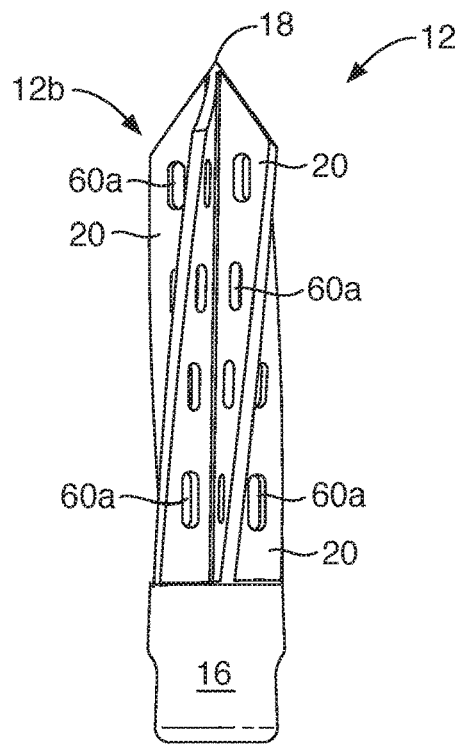
FIG. 7F is a side elevation view in a plane perpendicular to the curvature of the curved central axis.
Figure 7G:
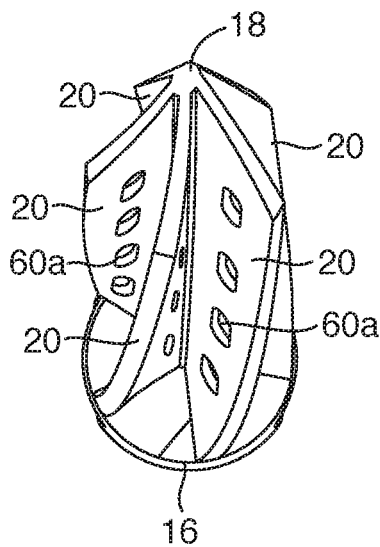
FIG. 7G is a cross-sectional view thereof taken near the distal end.
Figure 7H:
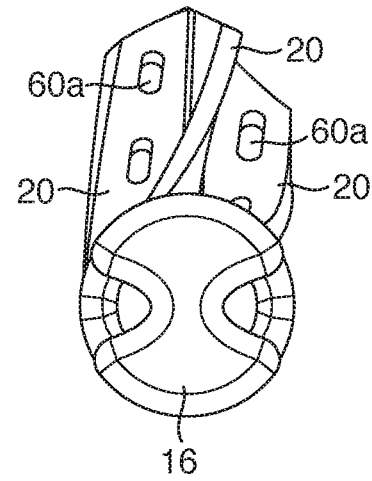
FIG. 7H is a cross-sectional view thereof taken at the proximal end thereof.
Figure 7J:
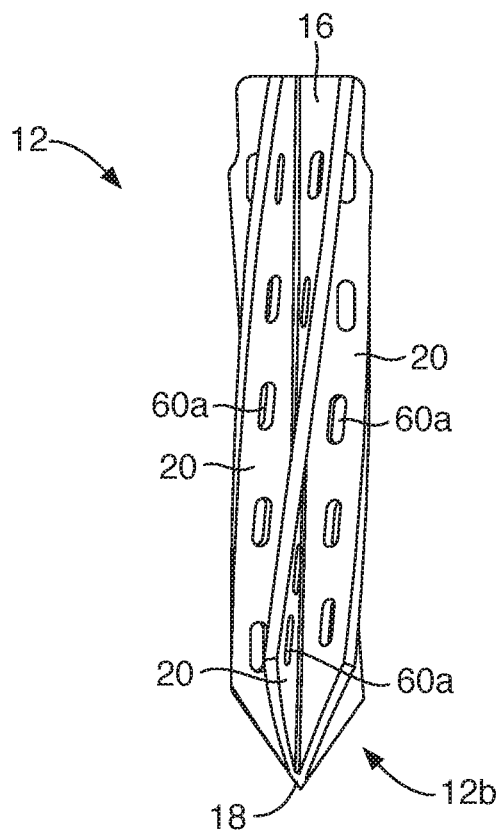
FIG. 7J is a side elevation view of an alternative embodiment of an anchor lacking a solid head with a circular or other cross-section, and therefore lacking a "bulkhead" at the proximal end of the splines to act as a stop in a frame or in cortical bone, and, being taken in a plane containing the curvature of the curved central axis through the anchor, corresponds to the view of FIG. 7E of the "headed" embodiment.
Figure 7K:
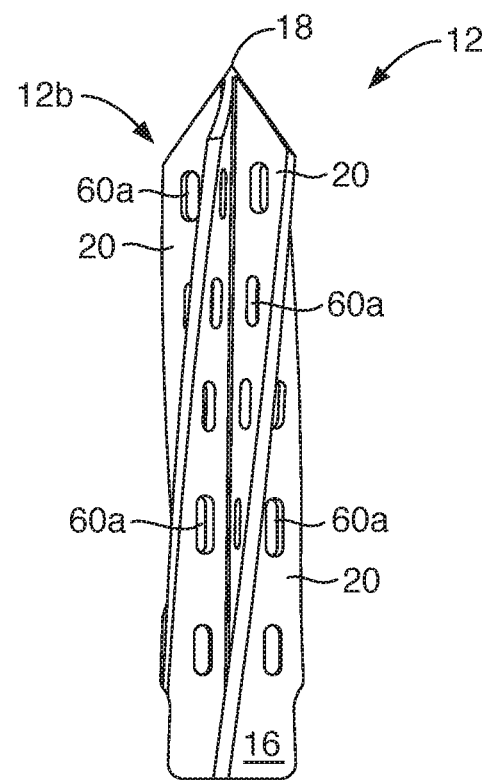

Referring to FIGS. 7J and 7K, all the foregoing information with respect to FIGS. 7A-7H may be applied in a more-or-less "headless" variety of anchor 12. In the illustrated embodiment, a tool may simply fit the splines 20 (in any embodiment of spline 20 discussed hereinabove) at a proximal end thereof. The tool may serve as the only "stop" for insertion of the anchor 12. In fact, a tool may be contemplated that would not present enough cross-sectional area perpendicular to the direction of motion to even operate as a stop.

For example, a tool may fit between the splines 20 like pieces of a pie divided by the splines. Alternatively, a tool may simply engage a few splines with thin clips leaving the space largely open between splines. All the features and function of this description of FIGS. 7J and 7K apply to hollowed anchors 12*b* as well as anchors 12*a*. Therefore an insertion tool may fit into the central aperture 22 at the proximal or "head 16" end, even without a solid head 16 other than what the splines 20 and wall 23 provide. Alternatively, note that trimming the outer diameter of the splines 20 may provide space to fit an insertion tool over the reduced diameter of splines, leaving a completely hollow center in the insertion tool.

In other embodiments, a distal end of an insertion tool may fit inside the aperture 22, with small fingers or simple interfering stubs extending outside the wall 23 and aperture 22. Those may engage splines to support rotational forces without presenting substantial resistance against the insertion tool following the anchor 20 as the anchor moves a distance longer than its length into or across a joint. Even the insertion tool may be cored (hollow), having a mere rim fitting inside and outside the aperture 22, and having slots to receive splines 20. Such a tool presents little more resistance to movement forward, permitting insertion along a path much longer than the anchor 20 itself. Thus longitudinal positioning of an anchor 20 need not be limited by a head 16 at a proximal end of the anchor 20.

Thus, for example, certain SI joint fusions relying on an anchor 12 passing somewhat parallel to the adjacent faces of the sacrum and ilius may rely on an insertion path longer than the anchor 12 itself. Neither the cortical bone nor the tool need stop the anchor, lacking a "bulkhead-like" face to stop forward progress of the distal (point 18) end.

In all of the foregoing discussion of surface roughness or "texturing," one should remember that shear forces along a slick, smooth, hard surface of a spline are going to be comparatively weak. On the contrary, just as apertures 60 engage tissues for through growth, texture provides concavities and convexities for "on growth." However, the surface shear forces (slip of any bone tissue with respect to a hard, artificial surface of an anchor 12) are augmented by local compressive and even tensile forces among texturing features. The presence of texturing provides immediate "purchase" or grip. Nevertheless, the adhesion and filling in by "on-growth" tissues engages the structure of the bone and projects or transfers true shear stress away from the anchor 12 and out into the tissues farther away but mechanical bound to the tissues grown onto the concavities and convexities of the texturing features.

Thus, in general, it is contemplated in a system and method in accordance with the invention that sintering, sputtering, casting, forging, printing, or other manufacturing techniques may be relied upon to provide not only through-apertures of any type (through tortuous paths of sintered grains of metal, for example, or formed as large open apertures 60 in splines), but surface texturing along any surface (inside, outside, etc.) of an anchor. The healing by macrophages in the first days after a surgery (and implant) will thus provide additional resistance to pull out, in addition to such compressive loading provided by the nature of the helical splines radiating outward from an arcuate "centerline" of an anchor 12.

In addition to tensioning of the anchor 12 providing compression in the tissue, the anchor provides a friction lock and a fast developing shear-engagement lock of the anchor 12 in place. That is, the tension in the anchor 12 due to its committing to a curvature of its centerline, and then being forced to rotate along the path of its helical splines, results in a compression of tissues behind (considering insertion path direction to be forward) the anchoring splines 20. Meanwhile, those splines 20, or rather their texturing will shear and smear tissues forward, which then engage immediately by friction against pull out. Healing then immediately begins to engage and lock in all that texturing, splines, and (apertures of every type) by intimate contact and growth filling concavities.

The present invention may be embodied in other specific forms without departing from its purposes, functions, structures, or operational characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by patent is:

1. A method comprising:
    providing an anchor characterized by a center curve formed in an arcuate shape defining at any point thereon an axial direction therealong, a radial direction perpendicular thereto, and a circumferential direction circumscribing therearound, the anchor having a head (proximal) end and a point (distal) end with splines extending helically therebetween and radially away from the center curve to define and fit within a diameter thereof;
    positioning the point end against a first bone structure;
    engaging the anchor by a tool urging the point end into the bone by imposing a first force upon the head; and
    fixing the anchor against withdrawal by progressing the anchor in the axial direction at the point end, guided by the splines along a combined arcuate direction along the center curve and helical direction along the splines.

2. The method of claim 1, wherein a head is formed at the head end absent splines extending therefrom, and the point end comprises a leading edge selected from a hollow point and a solid point.

3. The method of claim 2, comprising wherein the tool is capable of engaging the head to be capable of forcing the head in both the axial direction and circumferential direction thereat.

4. The method of claim 3, comprising urging the anchor to move in the axial direction at the point end by applying an impact load against the head.

5. The method of claim 4, comprising urging the anchor to twist along the direction of the splines during progressing forward by applying a circumferential force on the tool.

6. The method of claim 5, comprising providing a mallet capable of providing the impact load by a strike against the tool by the mallet.

7. The method of claim 1, comprising securing a second bone structure to the first bone structure by driving the anchor through the second bone structure before positioning the point end against the first bone structure.

8. The method of claim 1, comprising securing the first bone structure to a second bone structure by driving the anchor through the first bone structure and into the second bone structure.

9. The method of claim 8, comprising:
    providing a frame having apertures capable of receiving the anchor;
    fitting the frame between the first bone structure and the second bone structure; and
    passing the anchor through one of the apertures before positioning the point end against the first bone structure.

10. The method of claim 9 comprising:
    providing other anchors;
    passing the other anchors through others of the apertures; and
    securing the first bone structure and second bone structures to the frame and each other by driving at least one of the other anchors into the second bone structure.

11. An apparatus comprising:
    a head;
    a point;
    the head and the point each lying along a central axis characterized by an arcuate curvature curving continuously from the head to the point and defining a radial direction, proceeding orthogonally away therefrom, and a circumferential direction, circumscribing the central axis orthogonal to the radial direction throughout the length of splines of the apparatus; and
    the splines extending between the head and the point, each defining a helical direction progressing both axially along the central axis and radially away therefrom simultaneously at a pitch equal to multiple lengths of the anchor along the central axis.

12. The apparatus of claim 11, wherein the point is selected from a solid point, constituted by a convergence of the splines at a corresponding narrowing of a diameter of the apparatus, and a hollow point, constituted by a tubular structure from which the splines extend radially.

13. The apparatus of claim 12, wherein the head lacks splines extending radially therefrom.

14. The apparatus of claim 13, wherein the hollow point has a sharp edge capable of increasing stress on bone material by a reduction of a cross sectional area of the tubular structure.

15. The apparatus of claim 13, wherein the tubular structure is provided with grow-through apertures capable of fostering growth of bone material therethrough.

16. The apparatus of claim 11, wherein the splines are provided with grow-through apertures capable of fostering growth of bone material therethrough.

17. The apparatus of claim 11, wherein the apparatus is formed of a porous material capable of fostering growth of bone material therethrough.

18. An apparatus operable as an anchor capable of penetrating into bone, the apparatus comprising:
- a head and a point each lying along a central axis characterized by an arcuate curvature curving continuously from a head end to a point end to define an axial direction, a radial direction proceeding orthogonally away from the axial direction, while a circumferential direction circumscribes the central axis orthogonal to the radial direction at any location along the central axis; and
- splines extending radially away from the central axis, each extending between the head and the point in a helical direction progressing both axially along the central axis and circumferentially therearound at a pitch equal to multiple lengths of the anchor along the central axis.

19. The apparatus of claim 18, wherein:
- the point is selected from a solid point, constituted by a convergence of the splines at a corresponding narrowing of a diameter of the apparatus, and a hollow point, constituted by a tubular structure from which the splines extend radially, the tubular structure being provided with grow-through apertures capable of fostering growth of bone material therethrough;
- the splines are provided with grow-through apertures capable of fostering growth of bone material therethrough; and
- the apparatus is formed of a porous material capable of fostering growth of bone material therethrough.

20. The apparatus of claim 18, comprising a frame provided with anchor apertures capable of receiving and guiding a plurality of the anchors in directions capable of securing multiple bones to the frame and effecting through-growth between the multiple bones through the frame.

* * * * *